US008929967B2

(12) United States Patent
Mao et al.

(10) Patent No.: US 8,929,967 B2
(45) Date of Patent: Jan. 6, 2015

(54) NONINVASIVE SENSOR HOUSING

(75) Inventors: Jimmy Jian-min Mao, Fremont, CA (US); Robert E. Lash, Redwood City, CA (US)

(73) Assignee: ViOptix, Inc., Fremont, CA (US)

(*) Notice: Subject to any disclaimer, the term of this patent is extended or adjusted under 35 U.S.C. 154(b) by 1866 days.

(21) Appl. No.: 12/110,994

(22) Filed: Apr. 28, 2008

(65) Prior Publication Data
US 2009/0326354 A1 Dec. 31, 2009

Related U.S. Application Data

(63) Continuation-in-part of application No. 29/281,486, filed on Jun. 25, 2007, now Pat. No. Des. 567,949, and a continuation-in-part of application No. 29/303,969, filed on Feb. 21, 2008, now Pat. No. Des. 584,414.

(51) Int. Cl.
*A61B 5/1455* (2006.01)
*A61B 5/145* (2006.01)

(52) U.S. Cl.
CPC ....... *A61B 5/14551* (2013.01); *A61B 2562/185* (2013.01); *A61B 5/14532* (2013.01)
USPC ............ 600/344; 600/310; 600/322; 600/324

(58) Field of Classification Search
USPC .................................. 600/309–344
See application file for complete search history.

(56) References Cited

U.S. PATENT DOCUMENTS

| 4,674,512 | A | | 6/1987 | Rolf |
| D297,461 | S | | 8/1988 | Inoue et al. |
| 4,865,038 | A | * | 9/1989 | Rich et al. ..................... 600/344 |
| D327,739 | S | | 7/1992 | Anderson |
| 5,170,786 | A | * | 12/1992 | Thomas et al. ............... 600/310 |
| 5,217,013 | A | * | 6/1993 | Lewis et al. ................... 600/342 |
| D378,614 | S | | 3/1997 | Jensen |
| D385,037 | S | | 10/1997 | Jensen |
| 5,795,292 | A | * | 8/1998 | Lewis et al. ................... 600/323 |
| 5,797,841 | A | * | 8/1998 | Delonzor et al. ............. 600/323 |
| D457,634 | S | | 5/2002 | Rouns et al. |
| 6,516,209 | B2 | | 2/2003 | Cheng et al. |
| D477,085 | S | | 7/2003 | Sanfilippo |
| 6,587,703 | B2 | | 7/2003 | Cheng et al. |

(Continued)

OTHER PUBLICATIONS

Arbabi et al., "Near-Infrared Spectroscopy: A Potential Method for Continuous, Transcutaneous Monitoring for Compartmental Syndrome in Critically Injured Patients," Journal of Trauma, Nov. 1999, vol. 47, No. 3, pp. 829-833.

(Continued)

*Primary Examiner* — Eric Winakur
*Assistant Examiner* — Marjan Fardanesh
(74) *Attorney, Agent, or Firm* — Aka Chan LLP

(57) ABSTRACT

A flexible sensor pad includes a cavity to hold a sensor unit with an attached cable. According to one aspect of the present invention, a light-shielding layer is coupled to a bottom surface of the sensor pad, surrounds the sensor unit, and extends past two sides of the sensor pad. A transparent adhesive layer is coupled to the light-shielding layer and extends past two sides of the light-shielding layer. Another light shielding layer is coupled to a top surface of the sensor pad and covers the sensor unit. The cable divides the sensor pad into a first side and a second side which are mirror images of each other.

29 Claims, 14 Drawing Sheets

(56) References Cited

U.S. PATENT DOCUMENTS

| | | | |
|---|---|---|---|
| 6,597,931 | B1 | 7/2003 | Cheng et al. |
| D478,668 | S | 8/2003 | Epstein |
| 6,735,458 | B2 | 5/2004 | Cheng et al. |
| D495,055 | S | 8/2004 | Silber |
| D511,004 | S | 10/2005 | Masuda |
| D511,384 | S | 11/2005 | Masuda |
| 7,247,142 | B1 | 7/2007 | Elmandjra et al. |
| D561,900 | S | 2/2008 | Becsi |
| 7,355,688 | B2 | 4/2008 | Lash et al. |
| 2006/0258928 | A1 | 11/2006 | Ortner et al. |

OTHER PUBLICATIONS

Bellman et al., "Near-Infrared Spectroscopy Measurement of Regional Tissue Oxyhemoglobin Saturation During Hemorrhagic Shock," Shock, Sep. 1999, vol. 12, No. 3, pp. 196-200.

Cohn et al., "Tissue Oxygen Saturation Predicts the Development of Organ Dysfunction During Traumatic Shock Resuscitation," Journal of Trauma: Injury, Infection, and Critial Care, Jan. 2007, vol. 62(1), pp. 44-55.

Garr et al., "Monitoring for Compartmental Syndrome Using near-Infrared Spectroscopy:A Noninvasive, Continuous, Transcutaneous Monitoring Technique," Journal of Trauma, Apr. 1999, vol. 46, No. 4, pp. 613-618.

Gentilello et al., "Near-Infrared Spectroscopy Versus Compartment Pressure for the Diagnosis of Lower Extremity Compartmental Syndrome Using Electromyography-Determined Measurements of Neuromuscular Function," Journal of Trauma: Injury, Infection, and Critical Care, Jul. 2001, vol. 51, No. 1, pp. 1-9.

Giannotti et al., "Utility of Near-Infrared Spectroscopy in the Diagnosis of Lower Extremity Compartment Syndrome," Journal of Trauma: Injury, Infection, and Critical Care, Mar. 2000, vol. 48, No. 3, pp. 396-401.

Myers et al., "Noninvasive Method for Measuring Local Hemoglobin Oxygen Saturation in Tissue Using Wide Gap Second Derivative Near-Infrared Spectroscopy," Journal of Biomedical Optics, May/Jun. 2005, vol. 10(3), pp. 034017-1 to 034017-18.

Ward et al., "Near Infrared Spectroscopy for Evaluation of the Trauma Patient: A Technology Review," Elsevier Review Article, Resuscitation, 2006, 68, pp. 27-44.

\* cited by examiner

NONINVASIVE SENSOR HOUSING

CROSS-REFERENCE TO RELATED APPLICATIONS

This patent application is a continuation-in-part of U.S. design patent applications 29/281,486, filed Jun. 25, 2007, issued as U.S. design Pat. No. D567,949 on Apr. 29, 2008, and 29/303,969, filed Feb. 21, 2008, which are incorporated by reference along with all other references cited in this application.

BACKGROUND OF THE INVENTION

The present invention relates to medical devices and their manufacture. More particularly, the present invention relates to patient monitoring devices and methods.

Patient monitoring systems measure, display, and sometimes store physiological data. Patient monitoring systems are now used in a wide variety of applications. This includes, for example, hospital, ambulatory, and home health care. Hospitals routinely measure and analyze the vital signs of surgical, trauma, and other patients from admission through discharge. There are many different types of monitoring devices. For example, there are monitoring devices for blood pressure, body temperature, heart activity, blood gases, cholesterol, glucose, pulse rate, respiration rate, tissue oxygen saturation, and many other parameters.

Noninvasive monitoring devices fulfill an important role in assessing, tracking, diagnosing, and treating patients. These devices enable early diagnosis, treatment of acute conditions, and reduce the need for invasive interventions. Some types of monitoring devices gather patient data via sensors attached to the patient.

In order for the sensors gather accurate information, it is important that they are protected from outside interference. They should also be comfortable for the patient to wear as the sensors may be attached to the patient for long periods of time. Furthermore, anything that touches or comes near the patient must be sterile. Thus, sterility is also a concern. These are just a few examples of desirable features.

There is, then, a continuing demand for medical devices that are easier to use, safer to use, usable in locations outside the hospital, provide more features, and generally address the needs of patients, doctors, nurses, clinicians, first responders, and others in the medical community.

Therefore, there is a need to provide improved systems and techniques for monitoring patients.

BRIEF SUMMARY OF THE INVENTION

The present invention relates to patient monitoring devices. In an embodiment, the invention is a device that includes a pad region with a cavity, a first light-shielding layer, coupled to the pad region, where the first light-shielding layer has an opening that overlaps with at least a portion of the cavity, and an adhesive layer, coupled to the first light-shielding layer, where the adhesive layer extends past at least one edge of the first light-shielding layer.

The device may further include a sensor unit positioned in the cavity and a cable coupled to the sensor unit, where the cable is arranged to enter the cavity, the cable being arranged to define a longitudinal axis that passes through the cable and the device, dividing the device into a first side and a second side, where the first and second sides are mirror images of each other. The cable may have a length greater than 1.2 meters. The bottom surface area of the pad region may be greater than a bottom surface area of a sensor unit recessed into the cavity.

In an embodiment, the pad region, first light-shielding layer, and adhesive layer each include at least two opposing straight edges which are parallel, the pad region, first light-shielding layer, and adhesive layer being arranged so that the at least two opposing straight edges of the pad region, first light-shielding layer, and adhesive layer overlap, the adhesive layer further includes a left portion having a shape of a semicircle, a middle portion having a shape of a polygon, and a right portion having a shape of a semicircle, where the middle portion is between the left portion and the right portion.

The thickness of the pad region when uncompressed may be thicker than a sensor unit. A stiffener bar may be coupled to a top surface of the pad region, above at least a portion of the cavity. The device may further include a release liner, coupled to the adhesive layer, where the release liner includes a tab positioned along an edge where a cable enters the pad region. The adhesive layer may be transparent.

In an embodiment, the sensor unit includes a first source structure, a second source structure, a first detector structure include optical fiber, and a second detector structure including optical fiber. A first distance is between the first source structure and the first detector structure, a second distance is between the first source structure and the second detector structure, a third distance is between the second source structure and the first detector structure, a fourth distance is between the second source structure and the second detector structure. The first distance is not equal to the second, third, and fourth distances, the second distance is not equal to the third and fourth distances, and the third distance is not equal to the fourth distance.

In an embodiment, the device may further include a second light-shielding layer coupled to a top surface of the pad region, where the second light-shielding layer has an opening that overlaps with at least a portion of the cavity. A ratio of a thickness of the pad region to a length of the adhesive layer may be less than 0.1. The pad region may have a thickness at least about 3.2 millimeters. An edge of the cavity may overlap with an edge of the pad region.

In an embodiment, the device may further include a third light-shielding layer, where the third light-shielding layer includes a coupled portion and an uncoupled portion, where the coupled portion is coupled to the device and does not overlap the cavity, and the uncoupled portion overlaps the cavity.

In an embodiment, the invention is a device including a pad region with a cavity, a first light-shielding layer, coupled to the pad region, and an adhesive layer, coupled to the first light-shielding layer. A peripheral outline forms an outer boundary of the adhesive layer, and all points on a line drawn between any point on the peripheral outline to any other point on the peripheral outline are enclosed by the outer boundary.

The adhesive layer may further include a first convex edge, a second convex edge, a first straight edge, and a second straight edge. The first straight edge may be parallel to the second straight edge, the first and second straight edges may be between the first and second convex edges, and the first convex edge may be a mirror image of the second convex edge.

The device may further include a sensor unit positioned in the cavity, and a cable coupled to the sensor unit, where the cable has a length greater than 1.2 meters. Furthermore, the adhesive layer may be transparent.

In an embodiment, the invention is a device including a sensor unit, where the sensor unit includes a first source structure, a second source structure, a first detector structure, and a second detector structure. A cable is coupled to the sensor unit. The invention may further include a sensor pad, coupled to the sensor unit. The sensor pad includes a light-shielding layer coupled to a bottom surface of the sensor pad and extending beyond a first and second edge of the sensor pad in at least two opposite directions. An adhesive layer may be coupled to the light-shielding layer and extend beyond a first and second edge of the light-shielding layer in at least two opposite directions.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
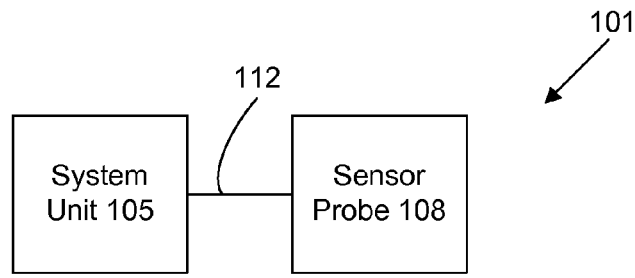
FIG. 1 shows an oximeter system for measuring oxygen saturation of blood in a patient.

FIG. 1 shows an oximeter system 101 for measuring oxygen saturation of blood in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers). In other implementations of the invention, however, connection 112 may be wireless such as via a radio frequency (RF) or infrared communication.

Typically, the system is used by placing the sensor probe in contact or close proximity to tissue (e.g., skin) at a site where an oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery, and patient monitoring such as during patient transport. Applications may also include use with intensive care patients, nursing home patients, and patients with acute illnesses. The tissue oximeter can make oxygen saturation measurements of tissue where there is no blood flow or pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbances of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
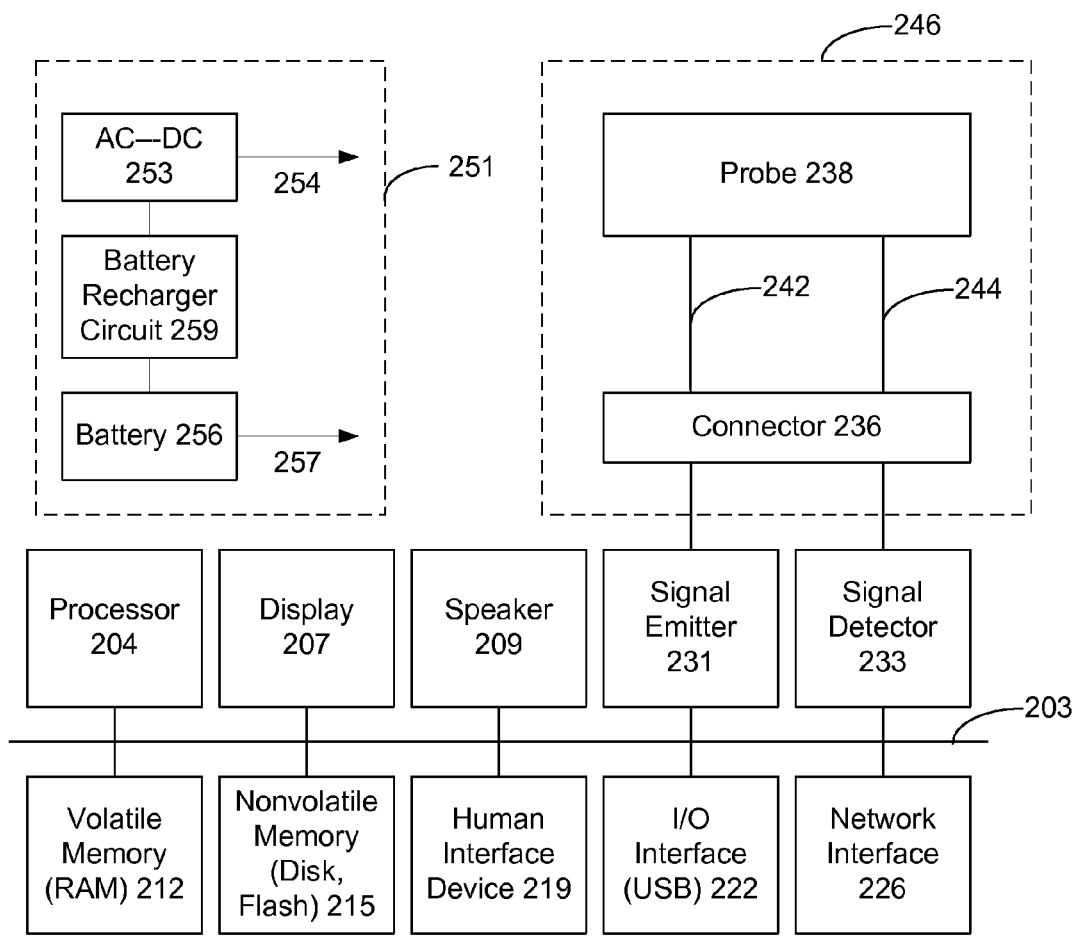
FIG. 2 shows in greater detail, a block diagram of a specific implementation of the system in FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only been inserted into a connector receptacle of the system unit in one or more specific orientations. This will ensure that proper connections are made.

The connector may also have a second keying feature that provides an indication to the system unit which type probe of probe is attached. The system unit may handle making measurements for a number of different types of probes. The second keying feature will let the system unit know which type of probe is connected, so that it can perform the right functionality, use the proper algorithms, or otherwise make adjustments its the operation for a specific probe type.

In various implementations, the system is powered using a wall outlet or battery powered, or both. Block 256 shows power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3:
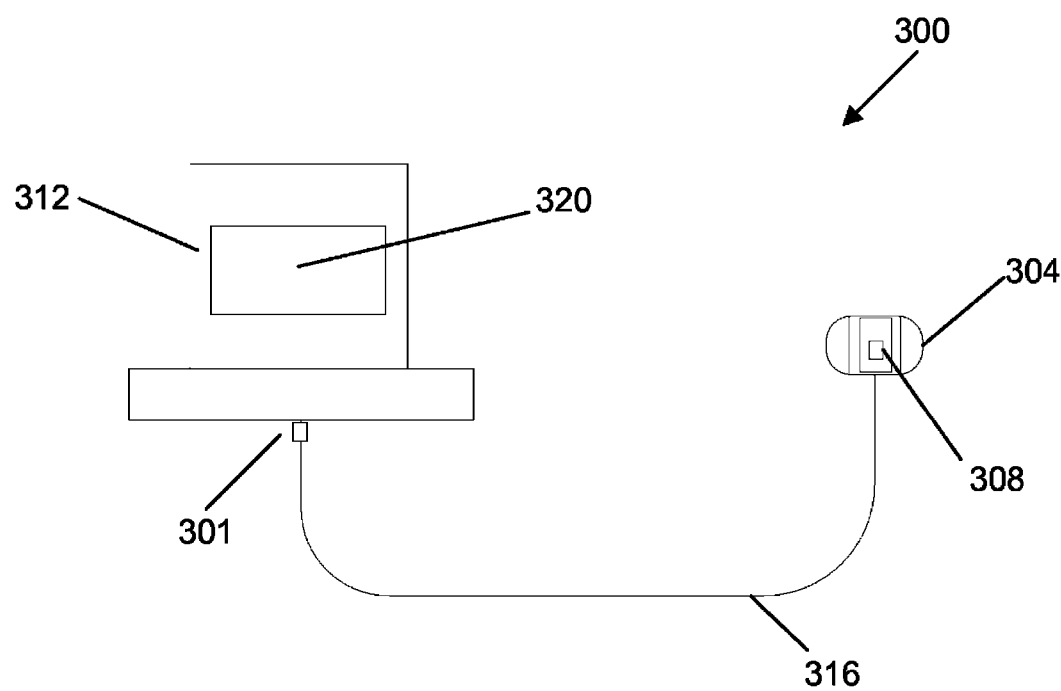
FIG. 3 shows an oximeter system that includes a console, cable, sensor unit and sensor housing in accordance with an embodiment of the present invention.

FIG. 3 shows a system 300 incorporating a sensor housing 304 with a sensor unit 308 of the invention. The system includes a monitoring console 312 and a cable 316. A connector 301 at an end of the cable connects the sensor unit to the monitoring console. The cable, connector, sensor unit, and sensor housing are disposable.

The length of the cable may vary. In a specific implementation, the length of the cable ranges from about 1.2 meters to about 3 meters. For example, the cable may be about 1.3, 1.4, 1.5, 1.6, 1.7, 1.8, 1.9, 2, 2.1, 2.2, 2.3, 2.4, or 2.5 meters long or greater. Depending on the specific application, the cable length may be less than 1.2 meters. In some applications, the cable length will be greater than 3 meters.

A specific application of the invention is operating room use or other places where it is desirable to maintain cleanliness and sterile conditions, such as isolation units. Patients in isolation units may have contagious diseases or compromised immune systems. Hospitals need to ensure that patients with a contagious disease do not infect others. Items introduced near the patient must either be disposed after use or properly cleaned. Hospitals also need to protect patients with compromised immune systems from sources of microorganisms. In these cases, a longer cable length, such as greater than 1.2 meters, is advantageous because this helps to separate the patient from sources of contamination, such as the console. Similarly, a longer cable length also minimizes contamination of, for example, the console by the patient.

The sensor housing, sensor unit, entire length of the cable, and the connector are packaged as a probe unit in a sterile package. The probe unit is detachable from the console after use and may be disposed. A user may then open a new sterile package containing a new probe unit. The package may be opened at the time of actual use or near the time of actual use so as to not contaminate the probe unit. The user can then connect this new and sterile probe unit to the console to begin monitoring. This disposable feature provides an additional level of protection in maintaining a sterile field around the patient.

Short cables may pose a problem. For example, short cables bring whatever element they are connected to within close proximity to the patient. Doctors and nurses must then devote additional care and time to ensure a sterile field around the patient. This may include, for example, additional cleansing of the elements before and after introduction to the sterile field, or sterile drapes on the elements.

In an implementation, the cable includes one or more optical wave guides enclosed in a flexible cable jacket. The optical wave guides may have the shape of a polygon, such as a square, rectangle, triangle, or other shape. In other cases, the optical wave guides may have circular or oval shapes.

In a specific implementation, the optical wave guides are multiple strands of fiber optic cable. The flexible cable jacket may be thin-walled PVC with or without an aluminum helical monocoil, shrink wrap tubing, plastic, rubber, or vinyl. In other implementations, however, the cable is standard electrical wiring (e.g., copper or aluminum wire), which is stranded or solid core, or coaxial cable, or any combination of these.

Further, the cable may also include a combination of one or more optical wave guides and electrical wiring. In a specific embodiment, the electrical wiring and each optical wave guide may be enclosed in their own separate flexible cable jacket. In another embodiment, multiple optical wave guides may be enclosed in a flexible cable jacket, separate from the cable jacket enclosing the electrical wiring. In yet another embodiment, both the optical wave guides and electrical wiring will be enclosed in the same flexible cable jacket.

In an implementation, the cable is passive. It does not contain any active, generative properties to maintain signal integrity. However, in other implementations, the cable includes active components. For example, the cable may amplify the signal at the sensor unit. Particularly long lengths of cable subject to significant attenuation may require amplification. Amplification may also be required if the monitored site contains a particularly dense structure such as bone.

In a specific embodiment utilizing multiple fiber optic cables, all of the fiber optic cables are enclosed within one end, or both ends of the flexible cable jacket. Minimizing the number of exposed cables lowers the likelihood that the cables will get entangled. In another embodiment, the fiber optic cables are not enclosed together and instead each fiber optic cable is enclosed in its own flexible cable jacket.

In an implementation, the cable and monitoring console have indicators. The indicators may be color indicators that are painted on, or raised indicators, or both. These indicators help the user to properly attach the cable to the monitoring console. For example, the indicators may include two green arrows placed on the cable and monitoring console, respectively. When the arrows are aligned the cable is properly attached. Further, there may be instructions printed on the console, cable, or both that instruct the user on the proper attachment of the cable to the console.

A coupling at the end of the cable attached to the monitoring console protects the cable from accidental disconnection. The coupling may be a threaded collar on a cable end that threads onto the monitoring console. Alternatively, the coupling may be a lug closure, press-fit, or snap-fit.

In an implementation, the console is portable. Thus, the console can be hand-carried or mounted to an intravenous (IV) pole. A portable console can follow a patient anywhere in the hospital, eliminating the need to change connections whenever a patient is moved. Moreover, a portable design facilitates use and assessments in numerous other locations besides a hospital.

A portable console is typically battery-operated. The battery is typically a rechargeable type, such as having nickel cadmium (NiCd), nickel metal hydride (NiMH), lithium ion (Li-Ion), lithium polymer, lead acid, or another rechargeable battery chemistry. The system can operate for a certain amount of time on a single battery charge. After the battery is drained, it may be recharged and then used again.

The portable console may also have a power-saving feature. This reduces battery consumption during continuous measurements. The power-saving feature may, for example, darken the console's display screen after a certain time of inactivity. The time may be approximately five, ten, fifteen, or twenty minutes. In an embodiment, the user may program the time.

In a specific implementation, the portable console weighs approximately 4.3 kilograms. However, the weight may vary from about 3 kilograms to about 7 kilograms including, for example, 3.5, 4, 4.5, 5, 5.5, 6, 6.5, or more than 7 kilograms. In other implementations, the weight may be less than 3 kilograms. The variation is due, in part, to the type of battery used in an implementation. For example, lead acid batteries are typically heavier and less compact, but less costly than NiCd or NiMH batteries. Thus, in an application where portability and size is a high priority such as in the small confines of a vehicle (e.g., ambulance) a lighter portable console may be used. However, where portability is a lower priority, such as in a hospital room, a heavier portable console may be used.

In another implementation, the console is not hand-held or portable. The console may be a large, nonportable device that is attached to a wall or secured to a stand or surface. In this implementation, the system is typically connected to AC power. A battery may be used as a back-up to the AC power.

In a specific implementation, the console provides alerts. The alerts may be visual (e.g., a flashing light on a display of the console), audible, or both. Visual alerts may be designed so that they are viewable from any location (e.g., flashing light on the top of the console). In a chaotic and noisy situation, this allows users to quickly respond to a patient. These alerts may signal a problem with the system. This includes, for example, insufficient signal strength, kinks or sharp bends in the cable, debris on the sensor unit, debris on a coupling surface between the cable and the console, insufficient electrical power, a low battery, an improperly attached cable, or other problem. An alert may also signal when the system is ready for patient monitoring. The alerts may also provide warnings at certain oxygen saturation levels. Different alerts may be used depending on the type of problem detected by the system. Different alerts include different colors, sounds, and intensities of colors and sounds.

The console may provide an alert when the sensor unit is placed in a suitable location for a measurement. The alert may vary in intensity depending on the suitability of the location. For example, a beeping sound may increase in frequency with more suitable locations. The alert may be audible, visual, or both. A benefit to an audible alert is that it allows the user to determine the suitability of a location without having to look away from the patient.

The alerts may be user-programmable. That is, users may, for example, set which alerts are enabled, the threshold at which they are activated, the intensities of the alerts, and more. For example, a user may decide to enable an oxygen saturation alert, set the alert to occur if and when the oxygen saturation level falls below a certain value, and set the volume level of the alert.

The console may also include a mass storage device to store data. Mass storage devices may include mass disk drives, floppy disks, magnetic disks, fixed disks, hard disks, CD-ROM and CD-RW drives, DVD-ROM and DVD-RW drives, flash and other nonvolatile solid-state storage drives, tape storage, reader, and other similar devices, and combinations of these.

The stored data may include patient information. This includes, for example, the patient's name, social security number, or other identifying information, oxygen saturation measurements and the time and date measured. The oxygen saturation measurements may include high, low, and average values and elapsed time between measurements.

The above drives may also be used to update software in the console. The console may receive software updates via a communication network such as the Internet.

In an implementation, the console also includes an interface for transferring data to another device such as a computer. The interface may be a serial, parallel, universal serial bus (USB) port, RS-232 port, printer port, and the like. The interface may also be adapted for wireless transfer and download, such as an infrared port. The system transfers data without interruption in the monitoring of the patient.

A screen 320 on the console displays the patient's data. The screen may be a flat panel display such as a liquid crystal display (LCD), plasma display, thin film transistor liquid crystal display (TFT LCD), electro-luminescent (EL), or organic light emitting diode (OLED) display. The screen may include a touch screen interface. Such touch screen interfaces are easier to clean compared to keypads if they become contaminated because they do not contain mechanical parts.

The screen may display numbers, text, graphics, and graphical trends in color. Different colors may correspond to different measurements or threshold levels. The text and numbers may be displayed in specific languages such as English, Spanish, French, Japanese, or Tagalog. The displayed language may be user-programmable.

Users can also vary the size of the displayed information on the console's screen. This allows the display to be viewed at a distance, increases the viewing angle, and allows users with vision limitations to see the information.

Figure 4:
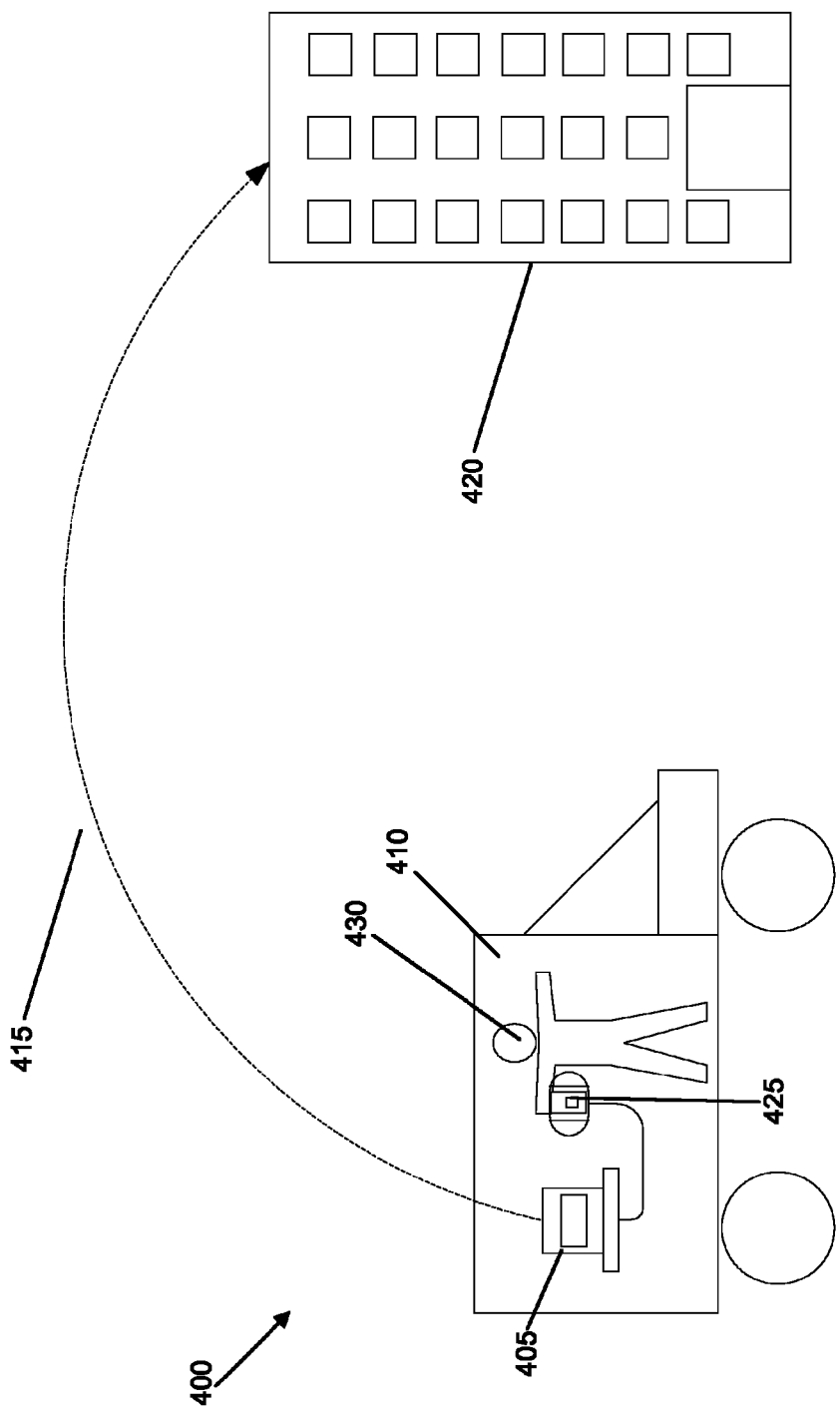
FIG. 4 shows the wireless transfer of patient data from a field location to a receiving location.

FIG. 4 shows an example of a wireless implementation of the invention. A system 400 includes a monitoring console 405 at a field location 410 which transmits 415 the patient's data to a receiving location 420. The figure shows the monitoring console transmitting the data, using for example, a modem in the monitoring console. However, in a different implementation, a sensor unit 425 may wirelessly transmit the data the receiving location.

In the figure, the field location is in an ambulance. The ambulance is transporting a patient 430 to a hospital. In other implementations, the field location may be in another type of vehicle such as a car, automobile, truck, bus, train, plane, boat, ship, submarine, or helicopter. The field location may also be on a battlefield, at an accident scene such as a car accident, at a natural disaster scene such as an earthquake, hurricane, fire, or flood, in a patient's home, at a patient's place of work, or in a nursing home.

The receiving location also varies. The receiving location may be a hospital, clinic, trauma center, physician's home or office, or a nurse's home or office. The monitoring console or sensor unit may also transmit to multiple receiving locations. For example, data may be transmitted to both the hospital and the physician's home.

A variety of devices may receive the data. This includes, for example, a monitoring console, other monitoring stations, mobile devices (e.g., phones, pagers, personal digital assistants or PDAs, laptops), or computers, or combinations of these.

The distance between the field and receiving location may vary. The field and receiving location could be in different countries, states, cities, area codes, counties, zip codes. In other cases, the field location and receiving location may be in different parts of the same room or in different rooms in the same building.

The wireless transmission may be analog or digital. Although FIG. 4 shows the system transmitting data directly to the receiving location, this is not always the case. The system may relay data to the receiving location using intermediaries. For example, satellites may rebroadcast a transmission. While in one embodiment, a communication network is the Internet, in other embodiments, the communication network may be any suitable communication network including a local area network (LAN), a wide area network (WAN), a wireless network, an intranet, a private network, a dedicated network, phone lines, cellular networks, a public network, a switched network, and combinations of these and the like. Wireless technologies that the system may employ include: Wi-Fi, 802.11a, 802.11b, 802.11g, 802.11n, or Bluetooth, or combinations of these and the like. The system also has the ability to switch from one communication technique to another if, for example, the current network is unreliable or there is interference. The switch may either be automatic or manual.

The system's ability to wirelessly transmit data offers several advantages. It reduces the time to treatment for a patient. For example, data sent from an ambulance en route to a hospital allows a physician at the hospital to mobilize personnel and equipment before the patient even arrives. Another advantage is long-distance monitoring. For example, patients may use the system in their own homes. The system will then, on a continuous basis if desired, transmit data to a receiving location, such as a hospital. A nurse or physician at the hospital can then review the data. If the data indicates a problem with the patient, then the hospital can dispatch an ambulance to the patient's home.

Figure 5:
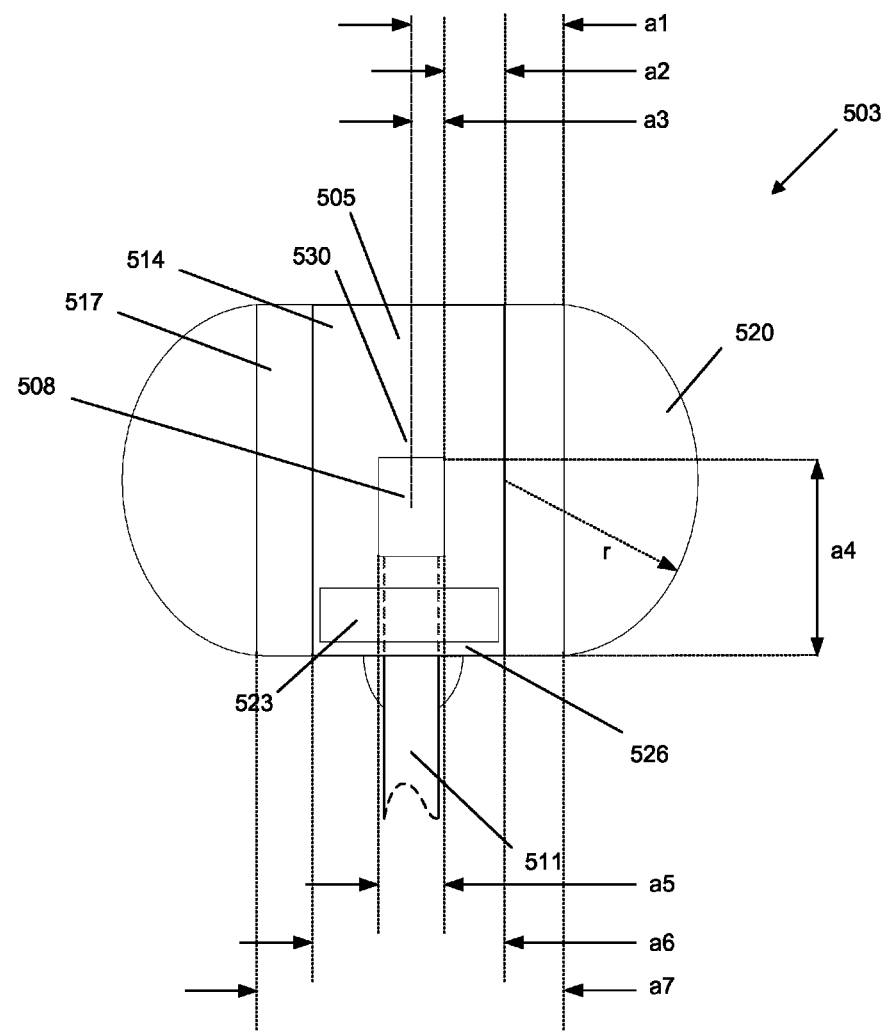
FIG. 5 shows a top side of a sensor housing in accordance with an embodiment of the present invention.

FIG. 5 shows a top side of a sensor housing 503 in accordance with an implementation. The sensor housing includes a cushioning layer 505 in which a sensor unit 508 is embedded. A cable 511 is coupled to the sensor unit. The cushioning layer is between a first light-shielding layer 514 and a second light-shielding layer 517. Though not shown in this figure, an additional third light-shielding layer may be above the first light-shielding layer. An adhesive film 520 with a release liner forms the base of the sensor housing.

A stiffener bar 523 may be attached near a bottom edge 526 of the sensor housing. In a specific embodiment, the stiffener bar may be approximately 0.76 to 1.27 millimeters from the bottom edge of the sensor housing. It may be approximately 0.51 to 1.52 millimeters from a side edge of the cushioning layer, including 1.02 millimeters. The stiffener bar may also be positioned on the bottom edge of the sensor housing. In a specific embodiment, the stiffener bar is placed above both the cushioning and light-shielding layers. In another embodiment, the stiffener bar is embedded within the cushioning layer, but above the cable. The common theme in all the embodiments is that the stiffener bar is placed above the cable.

The stiffener bar is typically a rigid material. In a specific implementation, the stiffener bar is polyester single coated with an adhesive film. In alternative embodiments it is made of other plastics such as other crystallized polymers (e.g., polypropylene or polyethylene) or other rigid material such as metal (e.g., steel or aluminum), carbon fiber, composites, nylon, ceramics, or cardboard.

The stiffener bar is optional. Embodiments not including the bar will not interfere with the functionality of the sensor housing. In an embodiment including the stiffener bar, the bar reduces the transmission of cable rotational torque to the sensor unit. It also reduces the movement of the sensor unit when the cable is pulled up perpendicularly to the patient's skin surface. The stiffener bar also helps when one tries to remove the sensor pad by pulling on the cable only. So the entire sensor pad will be lifted off instead of just having the sensor be pulled out of the sensor pad housing.

In a specific embodiment, the cushioning layer has the shape of a polygon. It may be made of foam, specifically, ⅛" (3.18 millimeters) thick cross-linked polyethylene foam coated on one side with a medical-grade adhesive (e.g. pressure sensitive medical-grade acrylic adhesive) with a white release liner (e.g., 92 pound, bleached kraft paper, poly-coated, silicone treated on one side), such as that made by Scapa North America of Windsor, Conn. and available as part no. 0399003. In this specific embodiment, thickness of the foam is determined under American Society for Testing Materials (ASTM) D1005-95.

In this specific embodiment, the adhesive properties may further include a thickness of 1.5 mils as determined under ASTM D1000-93, a value of tearing bond for adhesion to steel, and a value of tearing bond for adhesion to backing as determined under the Pressure Sensitive Tape Council (PSTC) test method number 1 with a 30 minute dwell time.

In other embodiments, the cushioning layer is polystyrene, paper, corrugated fiberboard, polypropylene, polyurethane, an inflated air pillow, silicon, latex, rubber, or molded pulp. The cushioning layer may have a 20 to 60 type A durometer.

The exact dimensions of the cushioning layer vary with the size of the embedded sensor unit. Typically, the cushioning layer, when uncompressed, is thicker than the thickness of the sensor unit in order to provide proper support. For example, if the thickness of the sensor unit is x, then the thickness of the uncompressed cushioning layer should be greater than x.

In an implementation, the bottom surface area of the cushioning layer is greater than the bottom surface area of the sensor unit. For example, the bottom surface area of the cushioning layer may range from approximately 200 to 700 percent greater than the bottom surface area of the sensor unit. This includes, for example, 225, 250, 275, 300, 325, 350, 375, 400, 425, 450, 475, 500, 525, 550, 573, 575, 600, 625, 650, or 675 percent greater.

In a specific implementation, the bottom surface of the sensor unit may be approximately 107.6 square millimeters and the bottom surface of the cushioning layer may be approximately 616.3 square millimeters. In a specific implementation, the cushioning layer is at least about 3.2 millimeters thick, 21.3 millimeters wide, and 38 millimeters long.

In an implementation, the cushioning layer is flexible. The flexibility allows the cushioning layer to conform to the shape of the sensor unit and the patient's skin. The result is that the sensor unit is shielded from ambient light. Source light is also prevented from escaping. The sensor unit uses light transmitted by an optical wave guide, such as a fiber optic cable, to obtain sensitive measurements. If light from the sensor unit escapes through the sensor housing, the sensor unit may not detect this light. Likewise, ambient light entering the sensor housing will also result in inaccurate readings. When the cushioning layer conforms it creates a dark environment within the sensor housing that enables accurate readings. The cushioning layer's flexibility is a function of its size and material type.

The implementation shown in FIG. 5 depicts a cavity in the cushioning layer. The cable enters the bottom edge of the cushioning layer through this cavity. The presence of the cavity provides additional flexibility to the cushioning layer.

The sensor unit is embedded in a cavity in the cushioning layer. This arrangement helps to maintain contact between the sensor unit's bottom surface and the skin of the patient. The sensor unit is generally embedded at or near a midpoint 530 of the cushioning layer. In this location, the cushioning and light-shielding layers surround the sensor unit to shield ambient light and contain the source light. However, in other implementations the sensor unit is embedded in other locations within the cushioning layer. In most embodiments it will not touch an outside edge of the cushioning layer. The portion of the cable that is coupled to the sensor unit is also embedded in the cushioning layer.

In a specific embodiment, the sensor unit is a part of the ODISsey™ Tissue Oximeter available commercially from ViOptix, Inc. of Fremont, Calif. ODISsey is a trademark of ViOptix.

A specific implementation may also include one or more light-shielding layers. For example, there may be one, two, three, or more than three light-shielding layers. In another implementation, the light-shielding layers may be omitted.

In an implementation, the light-shielding layers have the shape of a polygon. They are constructed of polypropylene film metalized with aluminum on the bottom side and coated with a pressure sensitive adhesive. In other implementations, the layers are made of a foil, a mirror, or made of other materials such as gold, titanium dioxide, or a composite of materials to block or reflect light. Other examples include a light-reflective tape, a material coated with light-shielding paint, a material impregnated with light-reflective material, or a light-reflective fabric. The sensor unit itself may be covered or made with a light-reflective material.

In an implementation, the first light-shielding layer has a shape that matches the top surface of the cushioning layer. That is, the first light-shielding layer has cavities that correspond to the cavities in the cushioning layer.

The second light-shielding layer has an opening that overlaps the sensor unit cavity in the cushioning layer. In an implementation, the second light-shielding layer is wider than the cushioning layer. It extends horizontally in equal portions beyond both sides of the cushioning layer. The total width of the second light-shielding layer may be approximately thirty to fifty-six percent greater than the width of the cushioning layer. The light-shielding layer can extend by a smaller or greater percentage as appropriate for the particular application.

The light-shielding layers serve several purposes. They prevent source light from escaping. They reduce ambient light. Placing the third light-shielding layer over the sensor unit and cable also secures the sensor unit and cable in their respective cavities in the cushioning layer.

In a specific embodiment, the adhesive film is matte finish, 3 mil transparent polyethylene, coated with a hypoallergenic, pressure sensitive acrylate adhesive. In other embodiments, the film is thicker or thinner, opaque or nontranslucent, or includes an alternative adhesive material (e.g., latex or silicone-based). The adhesive film may be a coating. The coating may be deposited using a brush or spray. The coating may be deposited as a series of small dots or lines. It may cover the entire bottom base of the sensor housing, or it may only cover a portion of the bottom base.

FIG. 5 also shows the symmetry of the sensor housing. The cable divides the sensor housing into two mirror images. Thus, the sensor housing is equally effective when it is used on either the right or left palms. Manufacturers can minimize their manufacturing costs because they do not need to manufacture left-handed or right-handed specific sensor housings.

Several dimensions are also shown in FIG. 5. Many other implementations are possible. These dimensions may vary considerably depending on the size of the tissue measured, the size of the sensor unit, or both. For example, infants require small sensor housings. In other cases, adults require large sensor housings. Table A below shows several implementations for the sensor housing dimensions.

TABLE A

| Variable | First Implementation (millimeters) | Second Implementation (millimeters) |
|---|---|---|
| a1 | 17.0 | 16.3-17.8 |
| a2 | 6.3 | 6.1-6.6 |
| a3 | 4.3 | 3.6-5.1 |
| a4 | 22.8 | 20.3-25.4 |

TABLE A-continued

| Variable | First Implementation (millimeters) | Second Implementation (millimeters) |
|---|---|---|
| a5 | 8.8 | 8.6-9.1 |
| a6 | 21.5 | 21.3-21.8 |
| a7 | 34.0 | 33.3-34.8 |
| r | 19.0 | 18.3-19.8 |

Figure 6:
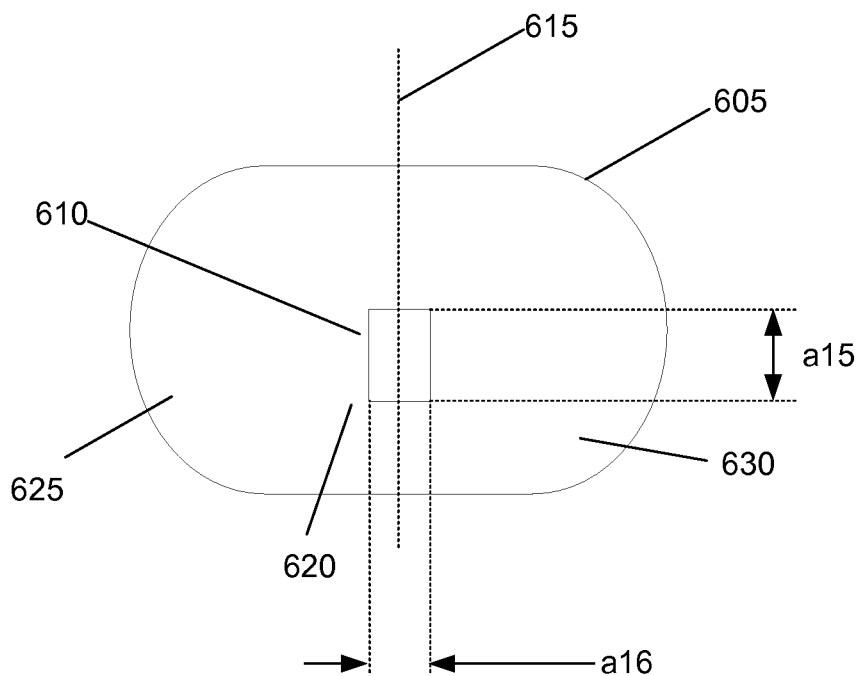
FIG. 6 shows an adhesive layer in accordance with an embodiment of the present invention.

FIG. 6 shows a specific implementation of the adhesive film. Here, the adhesive film has a convex shape defined by a peripheral outline 605. An opening 610 is provided for the sensor unit. Lengths a16 and a15 correspond to the width and length, respectively, of the opening. A line of symmetry 615 divides the adhesive film into two mirror images. A first portion 620 is located at the center of the adhesive film. Second and third portions 625 and 630 of the film extend horizontally from the first portion and line of symmetry.

The peripheral outline forms an outer boundary in which the opening is enclosed. All points on a line drawn between any point on the peripheral outline to any other point on the peripheral outline are enclosed by the outer boundary. Alternatively, the interior angle formed by any three points on the peripheral outline is not greater than 180 degrees. The convex shape as defined by the peripheral outline is independent of the shape of the opening. There may even be multiple openings. For example, the opening may have a convex or concave shape, the shape of a square, rectangle, circle, oval, triangle, crescent, or multiple combinations of these; the peripheral outline will continue to define a convex shape in which the outer boundary encloses these openings.

In the implementation shown, the adhesive film is roughly rectangular in shape with curved corners. Second and third portions have a semicircle, convex shape. Second and third portions lie on opposite sides of the first portion. Thus, the adhesive film resembles a rectangle with semicircles attached on opposite sides.

A convex shape has several advantages. For example, a user may be able to more easily remove the sensor housing from the patient as opposed to an adhesive film having a concave shape. This is because a concave shape has edges that curve inward resulting in interior angles. As the user peels away the sensor housing from the patient stress risers are formed at these interior angles. There is then a higher likelihood that the adhesive film will tear at these interior angles. The adhesive film must then be made stronger or thicker to resist tearing.

In another embodiment, the adhesive film has concave regions or a combination of concave and convex regions. These regions may be composed of straight line segments, convex line segments, concave line segments, or combinations of these. For example, an appendage such as a tab or multiple tabs may be attached to the peripheral outline. These tabs may aid in removal of the sensor housing by providing a place to grasp the adhesive film.

In a specific implementation, the second and third portions each extend approximately 12.7 millimeters beyond two edges of the second light-reflecting layer. In other implementations, these outer portions may be smaller or larger. Factors influencing the size of these outer portions include where on the body the user intends to place the sensor housing and the size of the sensor unit.

The width and length of the opening (i.e., a16 and a15) roughly correspond to the width and length of the sensor unit. In a specific implementation, width a16 may range from about 5 millimeters to about 11 millimeters. For example, a16 may be about 7, 7.1, 7.2, 7.3, 8, 8.1, 8.2, 8.3, 8.4, 8.5, 8.6, 8.7, 8.8, 8.9, or 9 millimeters long or greater. Depending on the specific application, the width may be less than 5 millimeters, or greater than 11 millimeters.

The length a15 may range from about 7 millimeters to about 13 millimeters. For example, a15 may be about 7.0, 7.1, 7.2, 7.3, 7.4, 7.5, 7.8, 7.9, 8, 9, 10, 11, 12.0, 12.1, 12.2, 12.3, 12.4, 12.5, 12.6, 12.7, 12.8, 12.9, or 13 millimeters long or greater. Depending on the specific application, the length may be less than 7 millimeters.

In a specific implementation, the area of the adhesive film is greater than the area of the opening. The area of the adhesive film may be about 14 to 18 times greater than the area of the opening. For example, the area of the adhesive film may be about 15, 16, 17, or more than 18 times greater than the area of the opening. Depending on the specific application, the adhesive film may be less than 14 times greater. In an implementation, the adhesive film has a surface area of approximately 1836 square millimeters and the opening has an area of approximately 109 square millimeters.

The adhesive film allows the sensor housing to adhere to the surface of the person, animal, or other living thing being monitored. Thus, it may be flexible and elastic so that it can conform to the surface. In an implementation, the adhesive film is nonirritating to the human skin. A user can remove the sensor housing without leaving any residue or causing any damage to the patient's skin. An adhesive film that is light-transparent, translucent, or semitransparent enables the clinician to observe the patient's skin color, temperature, and condition through the edges of the sensor housing.

In a specific embodiment, the adhesive film may be provided with a series of perforations. These perforations permit aeration of the skin. The aeration prevents the skin from becoming irritated, especially if the sensor housing is attached to the patient for a long period of time. The perforations also impart an additional degree of flexibility to the adhesive film. This too results in increased patient comfort.

In a specific implementation, the adhesive film may also be impregnated with antibiotics. This aids in preventing infections to sensitive skin.

Figure 7:
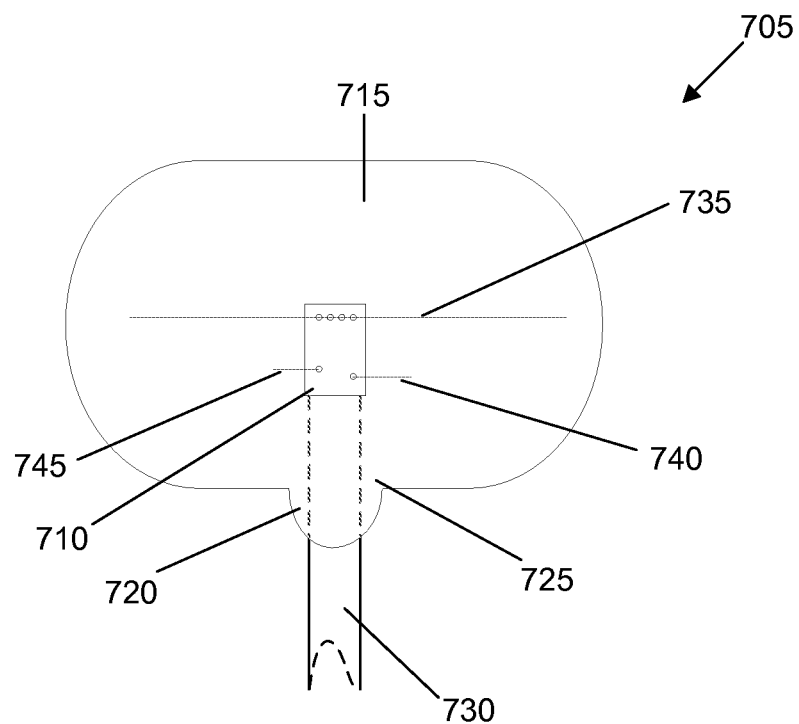
FIG. 7 shows a bottom side of a sensor housing in accordance with an embodiment of the present invention.

FIG. 7 shows a bottom side of a sensor housing 705 and sensor unit 710 in accordance with an implementation. A release liner 715 is coupled to the adhesive film on the bottom side of the sensor housing. A pull-tab 720 is attached to the release liner. The pull-tab is positioned at an edge 725 adjacent to a cable 730.

The bottom surface of the sensor unit is exposed. The bottom surface extends below the bottom side of the sensor housing in order to contact the tissue. Sensor openings along axes 735, 740, and 745 face away from the top of the sensor housing. Axes 740 and 745 pass through the source openings. Axis 735 passes through the detector openings.

FIG. 7 shows six openings for two sources and four detectors. However, a different number of openings are possible. In various specific implementations the sensor unit may have at least three openings for at least two source sensors and at least one detector sensor, or at least one source sensor and at least two detector sensors. There may be, for example, one, two, three, four, five, six, seven, eight, or more than eight sensor openings.

Although the sensor openings here are shown on different axes, the sensor openings may all be aligned along the same axis.

In a specific embodiment using fiber optic cables, one fiber optic cable connects to each opening on the bottom surface of the sensor unit. For example, if the bottom surface has six openings, there will be six fiber optic cables for transmitting optical information between the sensor unit and the monitoring console.

In an embodiment of the invention, each opening and corresponding fiber optic cable is dedicated to a particular purpose. For example, a first opening on the sensor unit (and corresponding fiber optic cable) is dedicated to transmitting light from the monitoring console. A second opening on the sensor unit (and corresponding fiber optic cable) is dedicated to transmitting a signal received at the second opening to the monitoring console.

Some embodiments use a particular opening and fiber optic cable for multiple purposes (e.g., both input and output) using a scheme such as multiplexing.

In a specific embodiment, a particular opening and cable transmits an output to affect a reaction (e.g., sending electrical signals to stimulate muscle or other tissue). Another opening and cable transmits the resultant signal back to the monitoring device. In yet another embodiment, the openings and cables may simply detect changes and transmit these changes back to the monitoring device. For example, the openings and cables may carry voltage changes in the patient's skin back to the monitoring device.

In an implementation, the sensor unit is passive. For example, it will not contain electrical circuitry or electrical devices, such as a power source, an amplifier, or photodiodes. A passive sensor unit may have openings, each opening holding an end of fiber optic cable. However, in other implementations, the sensor unit is active. It may, for example, contain an amplifier to amplify the signals in the sensor unit. In a specific embodiment, the sensor unit may contain photodiodes, including four photodiodes.

In one embodiment, the cable enters an edge of the sensor housing nearest the openings for the sources. In another embodiment, the cable enters an edge of the sensor housing nearest the openings for the detectors. In yet another embodiment, the cable enters an edge of the sensor housing mid-way, or part-way between the sources and detectors. Alternatively, the cable may enter from the top of the sensor housing.

The user removes the release liner to expose the adhesive film prior to adhering the sensor housing on the patient's skin. The release liner, in a specific embodiment, is a silicone treated, polyethylene coated, bleached kraft paper. In other embodiments, the liner is made of materials such as clay-coated paper, polycoated paper, polyester, or polypropylene, amongst others. It is treated with a material such as silicone to allow for easy removal from the adhesive film.

In a specific embodiment, the release liner is a single piece with a pull-tab to allow removal of the liner from the adhesive film in one piece. In this embodiment, the pull-tab is generally at the edge of the release liner closest to the cable. However, the pull-tab can be on other edges of the release liner. In another specific embodiment, the release liner is in multiple sections. For example, the release liner may be trisected to allow removal of the release liner in stages. Other embodiments could include fewer or more sections of liner, with or without pull-tabs. In lieu of or in addition to a pull-tab, the liner may be split to aid in removal of the liner from the adhesive film.

Figure 8:
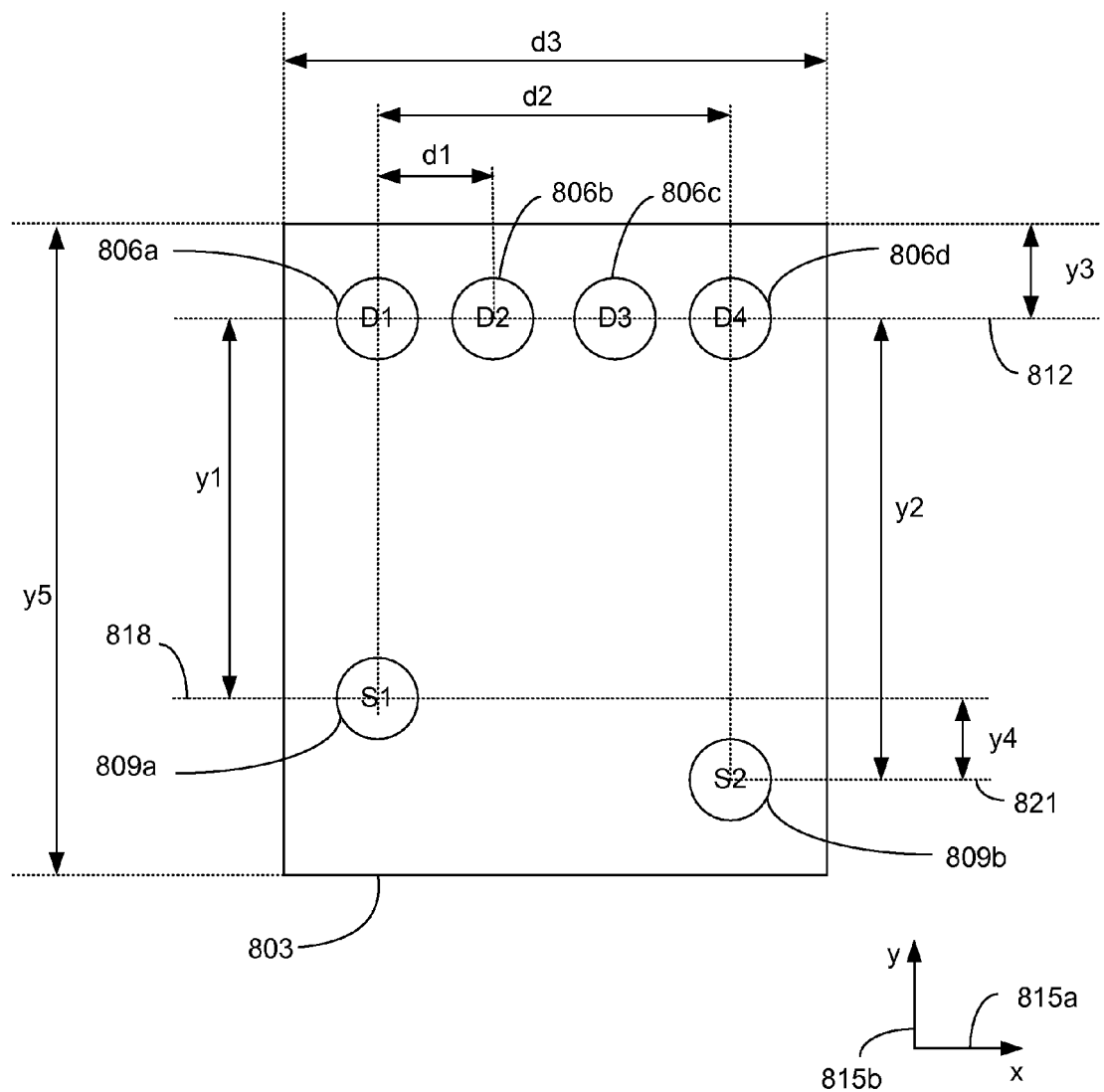
FIG. 8 shows a sensor unit with a pair of light sources that are in an offset arrangement relative to a set of four detectors in accordance with a first embodiment of the present invention.

FIG. 8 shows a sensor unit which is arranged to include a pair of sources or, more specifically, source arrangements and four detectors or, more specifically, detector arrangements, in accordance with an embodiment of the present invention.

A sensor unit 803 includes four detectors 806a-d and two sources 809a and 809b. Each source and detector has a reference point. The reference points may be the centers of the sources and detectors if, for example, the sources and detectors have circular shapes. Alternatively, the reference point may be defined as some other point, so long as the definition is consistent among the sources and detectors. A line 812 that is parallel to an x-axis 815a passes through a reference point for each detector.

Line 818 is parallel to x-axis 815a. Line 818 passes through a reference point of source 809a. Line 821 is parallel to x-axis 815a and passes through a reference point of source 809b.

In the described embodiment, a distance y1 along a y-axis 815b between line 812 and line 818 is different from a distance y2 along y-axis 815b between line 812 and line 821. It should be appreciated that distance y1 and distance y2 may vary widely depending upon any number of factors. The factors include, but are not limited to, the number of sources and detectors, the overall size of sources 809a, 809b and detectors 806a-d, the overall size of sensor unit 803, and the application for which sensor unit 803 is intended. While distance y2 is shown as being greater than distance y1, distance y1 may instead be greater than distance y2. In general, the difference between distance y2 and distance y1 is at least approximately 0.3 millimeters. For example, distance y2 and distance y1 may differ by approximately 0.5 or 1.0 millimeters.

The positioning of sources 809a, 809b and detectors 806a-d may vary widely. By way of example, sources 809a, 809b and detectors 806a-d are each approximately one millimeter in diameter. Sources 809a and 809b are directly below detectors 806a and 806d, respectively. In this example, sources 809a, 809b may be separated by a distance that is approximately 5 millimeters along the x-axis 815a, and by a distance y4 that is approximately 0.5 millimeters along the y-axis 815b, as measured from the reference point of each source. Detectors 806a-d may each be separated by approximately 1.7 millimeters along the x-axis, as measured from the reference point of each detector.

Table B below shows measurements for several implementations. Many other implementations are possible as explained above. In a first implementation, y1 is equal to d2.

TABLE B

| Variable | First Implementation (millimeters) | Second Implementation (millimeters) |
|---|---|---|
| y1 | 5 | 4.0-5.9 |
| y2 | 5.5 | 5.0-6.5 |
| y3 | 1.5 | 1.0-2.0 |
| y4 | 0.5 | 0.3-1.5 |
| y5 | 12.4 | 12.0-13.0 |
| d1 | 1.7 | 1.6-2.4 |
| d2 | 5 | 4.2-5.9 |
| d3 | 8.6 | 8.4-9.0 |

Sensor unit 803 is shown with a width of approximately 8.64 millimeters along x-axis 815a and a height of approximately 12.45 millimeters along y-axis 815b when detectors 806a-d and sources 809a, 809b are spaced as described in the first implementation above. However, sensor unit 803 generally has dimensions that may vary widely, e.g., dimensions which may vary depending upon the application for which sensor unit 803 is intended.

While a lack of symmetry in the positioning of sensors relative to detectors has been described as being such that distances between sensors and detectors are different relative to a y-axis, a lack of symmetry may instead or additionally have a lack of symmetry relative to an x-axis.

In a specific implementation, the source and detector structures comprise optical fiber. For example, one or more radiation sources may be located in the console. The optical fiber may then transmit the light from the console and through the source structures. The light, after having been transmitted through the patient's tissue, may then be received by the detector structures which transmit the received signal (i.e., light) back to photodetectors at the console.

In another implementation, the radiation sources, photodetectors, or both may be located at the sensor unit. For example, the source structures may include light-emitting diodes (LEDs) and the detector structures may include photodiodes.

In yet another implementation, the radiation sources may be located at the console, while the photodetectors are located at the sensor unit. In still another implementation, the radiation sources may be located at the sensor unit, while the photodetectors are located at the console.

Figure 9:
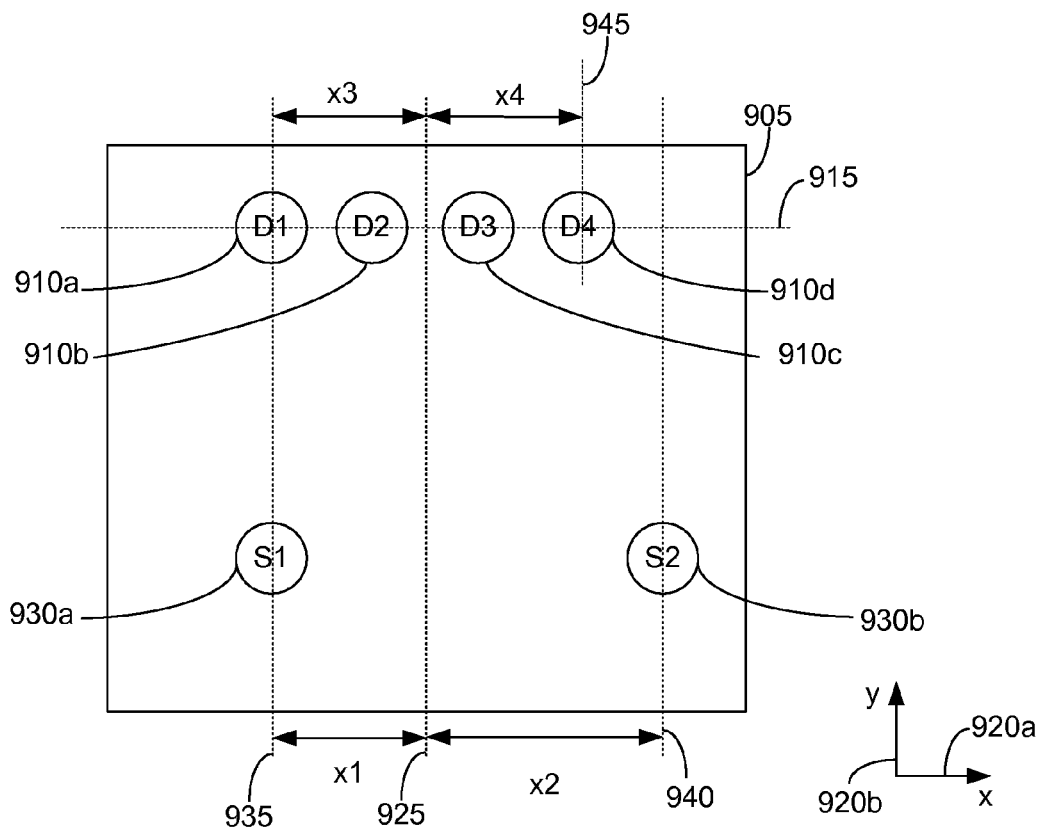
FIG. 9 shows a sensor unit with a pair of light sources that are in an offset arrangement relative to a set of four detectors in accordance with a second embodiment of the present invention.

Referring next to FIG. 9, a sensor unit that includes a pair of sources which are in an offset (or asymmetrical) arrangement relative to a set of four detectors with respect to an x-axis is described. A sensor unit 905 includes four detectors 910a-d, although the number of detectors 910a-d may vary. Detectors 910a-d are arranged such that a line 915 is substantially parallel to an x-axis 920a and passes through a reference point of each detector 910a-d. A first detector 910a and a last detector 910d, i.e., the detectors which are farthest apart relative to x-axis 920a, are used to define a central bisecting line 925 of detectors 910a-d. Central bisecting line 925 is parallel to a y-axis 920b, and is arranged such that a distance x3 from a reference point of detector 910a to central bisecting line 925 is substantially equal to a distance x4 from a reference point of detector 910d to central bisecting line 925. That is, central bisecting line 925 is arranged to pass through a central midpoint between detector 910a and detector 910d such that central bisecting line 925 is substantially perpendicular to line 915.

As shown, a reference point of first source 930a and a reference point of first detector 910a are aligned along a line 935 that is substantially parallel to a y-axis 920b. Similarly, a reference point of a second source 930b and a reference point of last detector 910d are aligned along lines 940 and 945, respectively, that are substantially parallel to y-axis 920b. It should be appreciated, however, that line 935 may not necessarily pass through the reference point of first detector 910a, and line 940 may not necessarily pass through the reference point of last detector 910d. That is, line 935 is effectively a line that is substantially parallel to y-axis 920b and passes through first source 930a, while line 940 is effectively a line that is substantially parallel to y-axis 920b and passes through second source 930b.

A distance x1 between line 935 and central bisecting line 925 is different from a distance x2 between line 940 and central bisecting line 925. In other words, first source 930a and second source 930b are not equidistant from central bisecting line 925. Hence, sources 930a, 930b are positioned in an offset or unbalanced orientation relative to x-axis 920a.

In yet another embodiment, the detectors may not be aligned on the same axis. For example, there may be rows of detectors where each row has a pair of detectors. The rows of detectors may be separated by a distance of approximately 10 millimeters. A pair of detectors in a row may be separated by a distance of approximately 5 millimeters. The distance from the sources to detectors may then vary between approximately 30 millimeters to 40 millimeters.

Although FIGS. 7, 8, and 9 show sources and detectors having circular-cross sections, in other implementations the cross sections have a different shape. These shapes may include convex and nonconvex shapes (e.g., a crescent shape), polygons such as a square, rectangle, or triangle, and combinations of these.

Each of the foregoing source and detector arrangements of the present invention may incorporate the source and detector arrangements discussed in U.S. Pat. No. 7,355,688, which is incorporated by reference.

Further in other implementations of the invention, the sensor unit has sensor openings arranged in a symmetrical or balanced arrangement. For one example of a symmetrical arrangement of sensor openings, the sensor openings are positioned at the corners of a rectangle, square, or other polygon where opposite sides have the same length.

In another example, the sensor openings are arranged so there is a first distance between a first detector and a first source and a second distance between the first detector and a second source, where the first and second distances are equal. In another example, the sensor openings are arranged so there is a first distance between a first source and a first detector and a second distance between the first source and a second detector, where the first and second distances are equal.

In another example, the sensor openings are arranged so there is a first distance between a first source and a first detector. There is a second distance between the first source and a second detector. There is a third distance between a second source and the first detector. There is a fourth distance between the second source and the second detector. The arrangement is symmetrical when the first distance is equal to the fourth distance, and the second distance is equal to the third distance.

FIGS. 10-14 show cross-sectional views of the sensor housing in accordance with several embodiments of the present invention. The layers shown are not drawn to scale to allow easier visual differentiation of the layers within the figure's representation.

Figure 10:
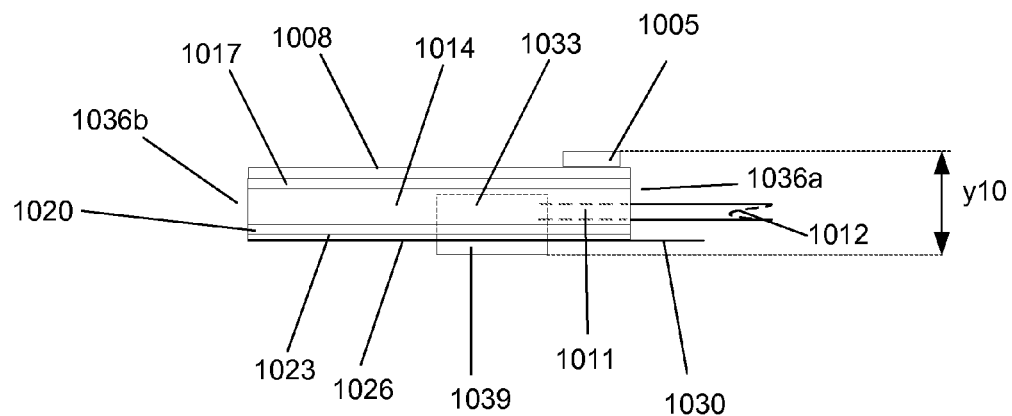
FIG. 10 shows a cross-sectional view of a sensor housing where a cavity in a cushioning layer for a cable is located between the top and bottom surfaces of a cavity for a sensor unit in accordance with a first embodiment of the present invention.

In FIG. 10, a stiffener bar 1005 is above a third light-shielding layer 1008 and cavity 1011. A cushioning layer 1014 is between a first light-shielding layer 1017 and a second light-shielding layer 1020. An adhesive film 1023 is coupled to the second light-shielding layer. The adhesive film is covered by a release liner 1026 which has a pull-tab 1030. The release liner is on a bottom side of the sensor housing. In an alternative implementation, the stiffener bar is embedded in the cushioning layer below the second light-shielding layer, but above the cable. In other implementations, the stiffener bar is absent, or the second light-shielding layer is absent, or both the stiffener bar and the second light-shielding layer are absent.

The cushioning layer contains a cavity 1033. Cavity 1033 is located between an end of the cushioning layer 1036a and an opposite end of the cushioning layer 1036b. The cavity may be a slot, recess, hole, hollow area, divot, pocket, chamber, or other space. In a specific embodiment, the cavity may be partially enclosed by the cushioning layer. For example, the cavity may be enclosed by three portions of the cushioning layer. In another embodiment, the cavity may be completely enclosed by the cushioning layer.

Cavity 1033 conforms to the shape of sensor unit 1039. An edge of the sensor unit is generally midway between the ends of the cushioning layer, though it may be offset from the mid-point in an implementation.

The sensor unit is held in cavity 1033 with an adhesive. The bottom surface of the sensor is exposed through the cavity, the second light-shielding layer, and the adhesive film. In a specific implementation, the bottom surface of the sensor is also exposed through the release liner. The bottom surface of the sensor unit may protrude past the bottom of the sensor housing from about 0.8 millimeters to about 2 millimeters. For example, the bottom surface of the sensor unit may protrude about 0.9, 1.0, 1.1, 1.2, 1.3, 1.4, 1.5, 1.6, 1.7, 1.8, or 1.9 millimeters or greater.

Exposing the bottom surface of the sensor unit past the bottom surface of the sensor housing ensures that the sensor unit properly contacts the tissue to be monitored. It also allows preliminary measurements of the proposed site before the sensor housing is attached to the patient. In another implementation, the bottom surface of the sensor unit is covered by the release liner. This protects the sensor unit from debris.

Cavity 1011 in the cushioning layer is coupled to cavity 1033. Cavity 1011 is intended for a cable 1012. The cavity may be a slot, recess, hole, hollow area, divot, pocket, or other space partially enclosed by the cushioning layer. This particular figure shows cavity 1011 between the top and bottom surfaces of cavity 1033. In an implementation, cavity 1011 has a greater volume than cavity 1033. In other implementations, the volume of cavity 1011 is less than the volume of cavity 1033. In a specific implementation, the cavities have the same width.

The cable enters through an edge of the cushioning layer and into cavity 1011. The cable enters the cushioning layer at an end 1036a above the release liner, the adhesive film, and the second light-reflecting layer. The cable connects to the sensor unit at the bottom edge of the sensor unit, at the top edge of the sensor unit, or between the bottom and top edge of the sensor unit.

FIG. 10 also shows dimension y10 which is the overall thickness of an implementation. In the specific implementation y10 is about 4 millimeters. However, the thickness may vary. It may be from about 3 millimeters to 15 millimeters or greater. For example, the thickness may be 4, 5, 6, 7, 8, 9, 10, 11, 12, 13, 14, or 15 millimeters long, or greater. Factors influencing the thickness include the presence or absence of certain items from various embodiments. For example, in an embodiment where the stiffener bar is absent or embedded in the cushioning layer the thickness will be smaller. In another embodiment, a different sensor unit may be used that contains, for example, photodetectors or other electronic circuitry to obtain measurements through deeper structures. In that embodiment, the overall thickness of the implementation will be greater.

A ratio of the sensor housing's thickness to its overall length, i.e., aspect ratio, ranges from about 0.03 to about 0.20. For example, the aspect ratio may be about 0.04, 0.05, 0.06, 0.07, 0.08, 0.09, 0.1, 0.2, 0.3, 0.4, or greater than 0.4, or less than 0.03. In a specific implementation, the sensor housing has a thickness of about 4 millimeters and an overall length of about 59.4 millimeters. The overall length is the longest distance between two opposite points on the sensor housing. This yields an aspect ratio of about 0.07.

Thinner implementations benefit from being less obtrusive. There is less likelihood that the device will be accidently jarred causing inaccurate results. The patient also feels less of a "tugging" sensation. This is because the device sits closer to the patient's skin which lessens the amount of torque on the device due to gravity.

FIGS. 11 to 14 show cross-sectional views of several different implementations of the cavity for the sensor unit and the cavity for the cable.

Figure 11:
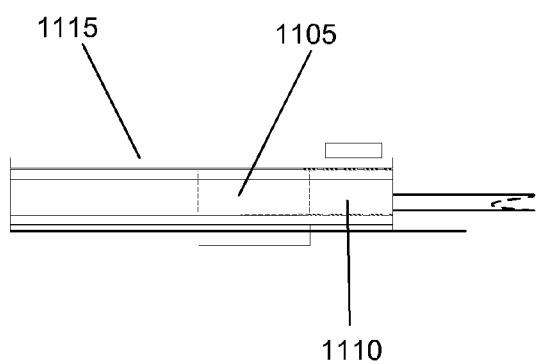
FIG. 11 shows a cross-sectional view of a sensor housing where cavities for a cable and a sensor unit have the same thickness as a cushioning layer for the sensor unit in accordance with a second embodiment of the present invention.

FIG. 11 shows depths of cavities 1105 and 1110 having the same thickness as the cushioning layer. Thus, when viewing the cushioning layer from the top, the cavities appear as a slot. The cavity is bounded on three sides by the cushioning layer. In other implementations, the cavities may be fully surrounded by the cushioning layer. Light-shielding layer 1115 has an adhesive and covers the cushioning layer, sensor unit, and cable. The adhesive secures the sensor unit and cable in their cavities.

Figure 12:
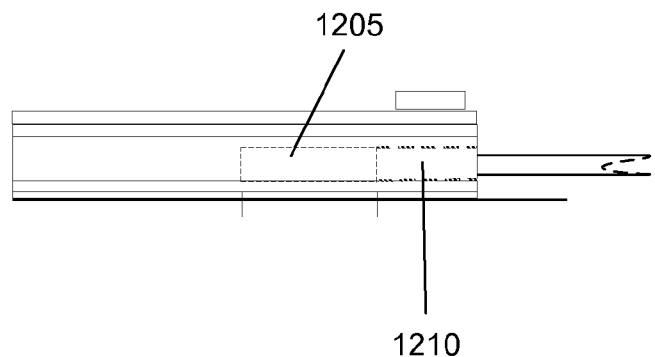
FIG. 12 shows a cross-sectional view of a sensor housing where cavities in a cushioning layer for a sensor unit and a cable have the same depth in accordance with a third embodiment of the present invention.
Figure 13:
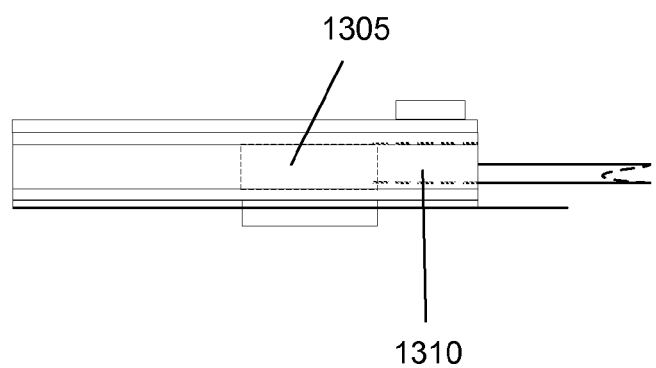
FIG. 13 shows a cross-sectional view of a sensor housing where top surfaces of cavities for a sensor unit and a cable are on the same plane in accordance with a fourth embodiment of the present invention.
Figure 14:
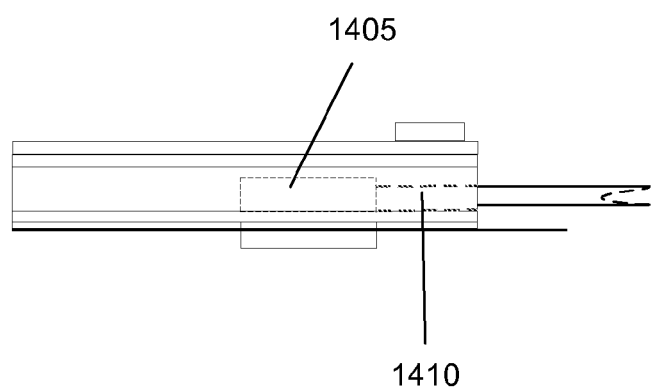
FIG. 14 shows a cross-sectional view of a sensor housing where bottom surfaces of cavities for a sensor unit and a cable are on the same plane in accordance with a fifth embodiment of the present invention.

In FIG. 12, cavities 1205 and 1210 have the same depth, but the depth is less than the thickness of the cushioning layer. In FIG. 13, the top surface of cavity 1310 is on the same plane as the top surface of cavity 1305. The figure also shows cavity 1305 having a greater depth than cavity 1310. In FIG. 14, the bottom surface of cavity 1410 is on the same plane as the bottom surface of cavity 1405. The figure also shows cavity 1405 having a greater depth than cavity 1410.

Figure 15:
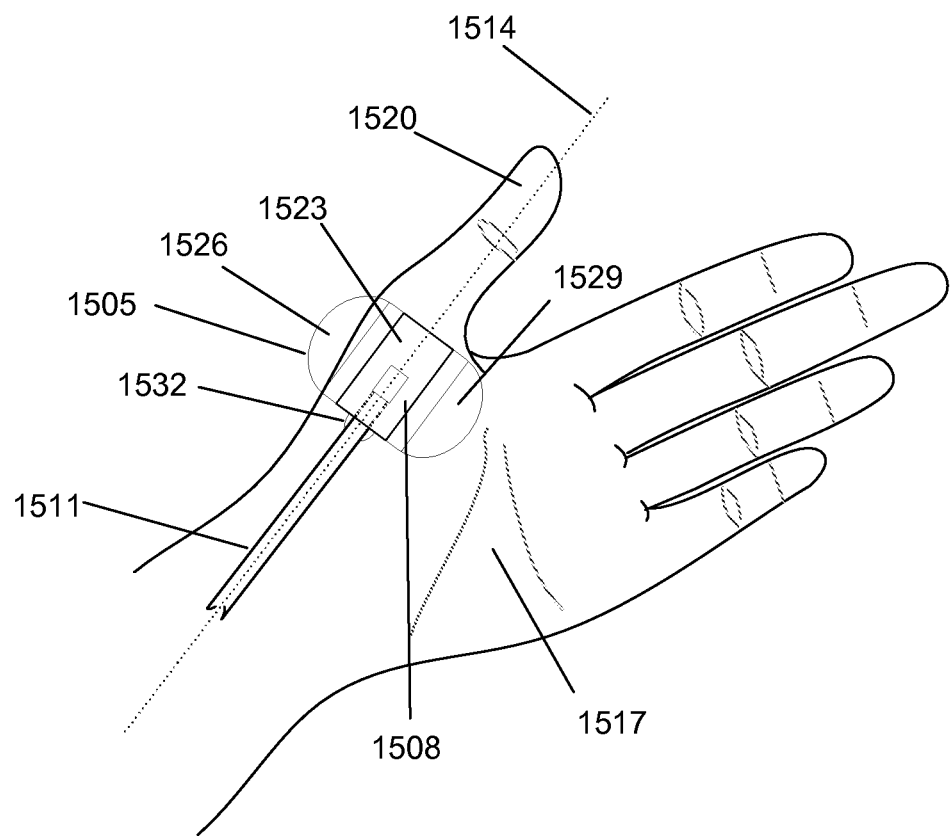
FIG. 15 shows a sensor housing placed on a patient's palm in accordance with a first embodiment of the present invention

FIG. 15 shows a sensor housing 1505 on a patient's thenar eminence 1508. Cable 1511 is positioned along axis 1514 which is located on a patient's open palm 1517. The axis runs through the thenar eminence and a thumb 1520. In this particular implementation, the adhesive film includes a three-section release liner, including first (or center), second, and third portions 1523, 1526, and 1529, respectively. Pull-tab 1532 is attached to the first portion of the release-liner.

Measuring tissue oxygen saturation at the thenar eminence provides several benefits. First, the measurement may be used to predict the development of organ dysfunction during traumatic shock. For example, as traumatic shock begins, peripheral vasoconstriction directs blood away from the limb muscles into the brain. This causes a drop in peripheral muscle tissue oxygen saturation. Medical personnel may then intervene with resuscitation efforts. Second, measurement may be used to determine when resuscitation is successful. For example, as the shock ends, blood to the internal organs is restored first, followed by blood to the muscles.

Typically, when using near-infrared spectroscopy to measure tissue oxygen saturation at the thenar eminence, the near-infrared radiation is calibrated to penetrate the tissue at a depth of approximately five millimeters. However, the depth may vary depending if a measurement is taken at a different location. For example, if the tissue to be measured is below structures such as bone or layers of adipose tissue, then the near-infrared radiation may be calibrated to penetrate deeper such as 6, 7, 8, 9, 10, 11, 12, 13, 14, 15, or more than 15 millimeters.

Figure 16:
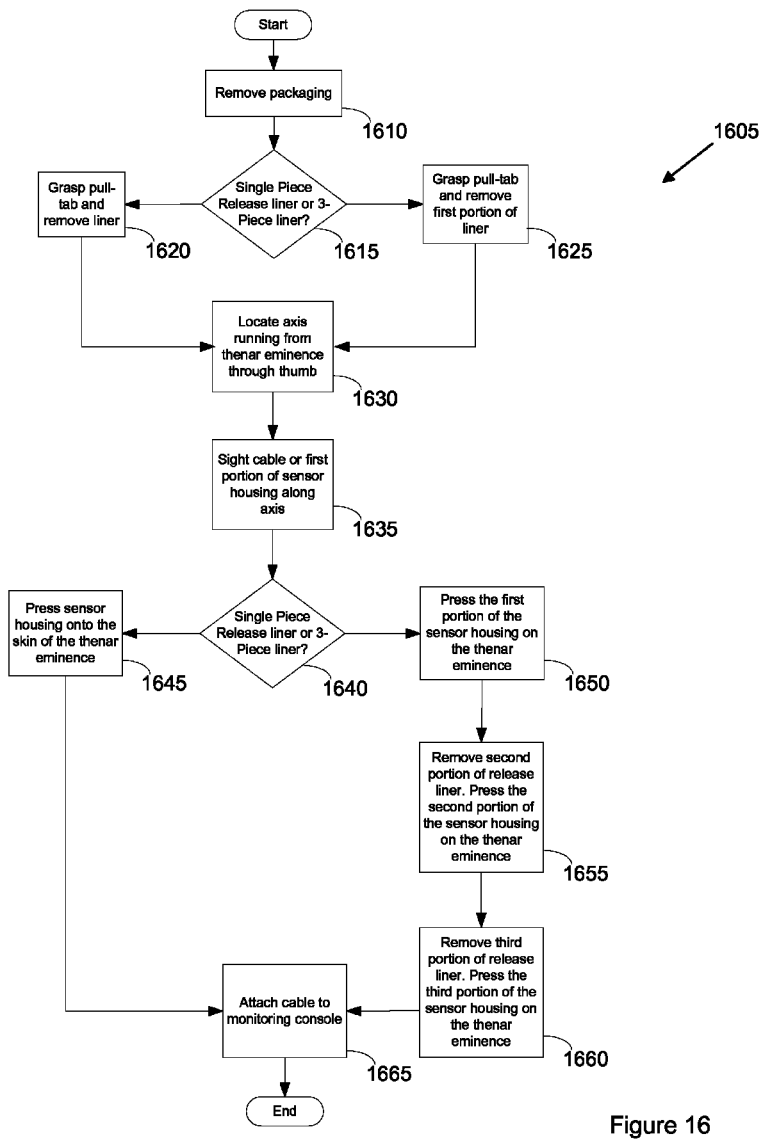
FIG. 16 shows a process flow of using a sensor housing in accordance with a first embodiment of the present invention.

FIG. 16 shows process flow 1605 which is an application of the sensor housing in accordance with an embodiment of the present invention. No threshold readings are required prior to taking a measurement. In a specific application, the user monitors the tissue oxygenation saturation of the thenar eminence, which may assist medical personnel in monitoring shock-associated hypoperfusion.

In a step 1610, the user removes the sensor housing, and sensor unit with its attached cable, from the packaging. The cable is generally flexible. Thus, the user can arrange the cable so it creates a straight line near its entry to the sensor housing.

In a step 1615, the user either removes the entire release liner (a step 1620) if it is a single-piece liner or just the first (or center) release liner (a step 1625) if it is a multipiece release liner. The user removes the release liner by grasping the cable with one hand and pulling on the pull-tab with the other hand. This exposes the adhesive. The user then adheres the sensor housing to the patient.

In a step 1630, the user locates the axis running from the patient's thenar eminence through the thumb. Next, in a step 1635, the user aligns the sensor housing along that axis. In an implementation, figures and text on the sensor housing, or cable, or both instruct the user on how to properly position the sensor housing. For example, an arrow may be painted in the middle of the sensor housing. Printed instructions may direct the user to point the arrow towards the base of the patient's thumb.

In an alternative implementation, the user may also use the cable as a sight. For example, the user first finds the axis along the thenar eminence by sighting from the patient's open palm and through the thenar eminence and thumb. The user can use the cable, since it resembles an axis itself, as sight to align the sensor unit over the thenar eminence. In other embodiments measuring the oxygen saturation of other tissues, the user similarly positions the cable so that it runs generally along an axis of the tissue.

In a step 1640, the release liner is either a single-piece or a multipiece release liner. If the release liner is a single-piece liner then the user presses the entire sensor housing onto the skin of the thenar eminence, a step 1645. If, however, the release liner is a multipiece release liner, for example, a three-piece release liner, then the user presses the first portion of the sensor housing onto the skin of the thenar eminence, a step 1650. In a step 1655, the user removes a second release liner. The user then presses the second portion of the sensor housing onto the skin to conform the sensor housing to the patient's body. The user repeats this process in a step 1660 with the third portion of the sensor housing.

Finally, in a step 1665, the user attaches the cable to the monitoring console. The user may disconnect the cable from the monitoring console and reconnect it to the same or a different monitoring console without calibration. Alternatively, the user may attach the cable to the monitoring console as a preliminary step. This allows a preliminary measurement of the proposed site before affixing the sensor housing to the tissue.

Figure 17:
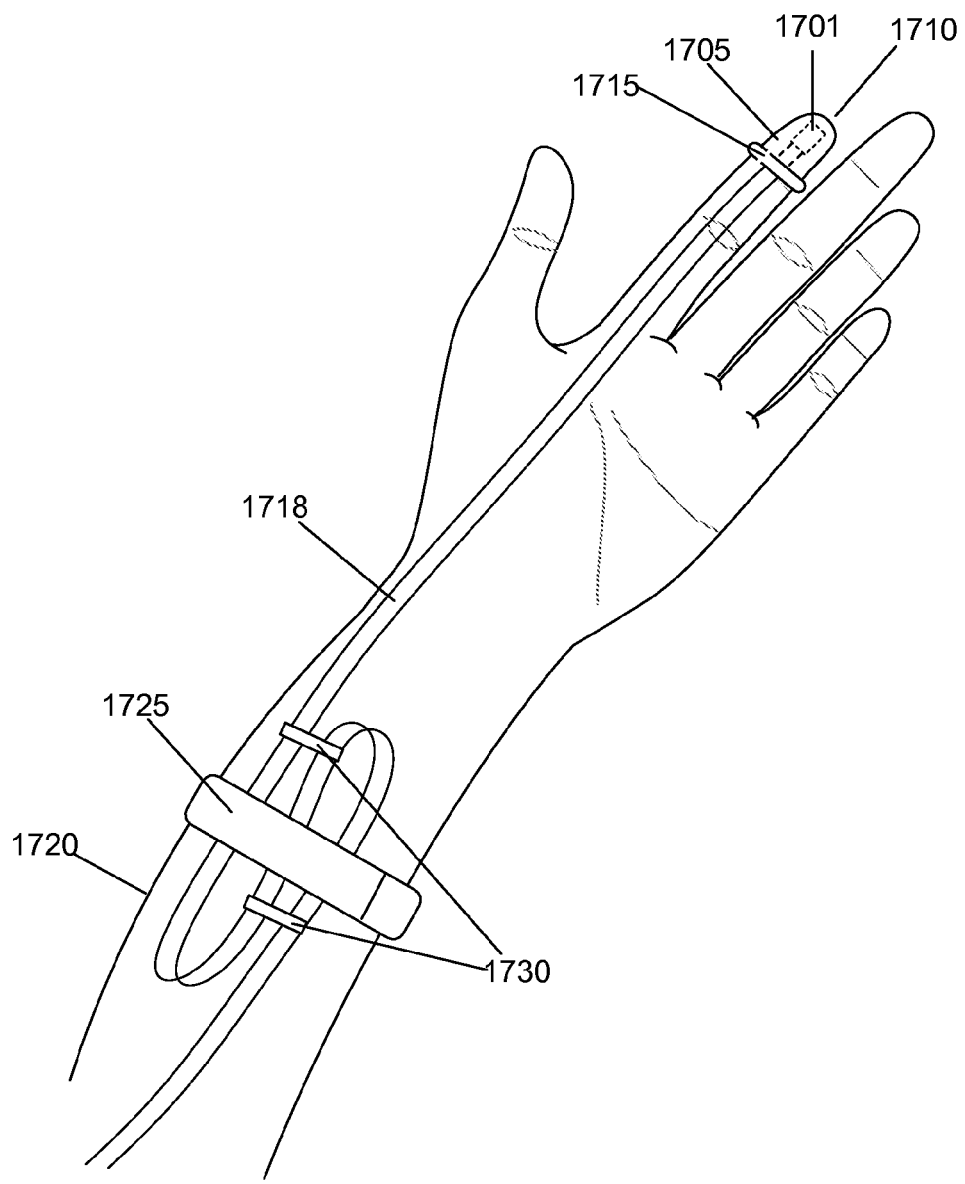
FIG. 17 shows a sensor unit placed on a patient's fingertip in accordance with a second embodiment of the present invention.

FIG. 17 shows an alternative implementation where the user attaches a sensor unit 1701 without the sensor housing. In this implementation, the sensor unit is not embedded within the sensor housing. Instead, it is left exposed on all sides. Using the sensor unit without the sensor housing may be more appropriate in certain trauma situations where use of the sensor housing is contraindicated. Separate material, not coupled to the sensor unit, is used to create a sensor housing to secure the sensor unit. In this example, a finger glove 1705 secures the sensor unit on a patient's fingertip 1710. A ring 1715 on the finger glove is cut to reduce constriction. Cable 1718 runs along a patient's forearm 1720. The cable attaches to the forearm with a strap 1725. Ties 1730 provide additional strain-relief for the cable.

In an implementation, the finger glove is a latex finger cot. In other implementations, the finger glove is made of nitrile rubber, vinyl, cloth, or other flexible materials. In an implementation, the finger glove has an inner diameter in the range of 18-22 millimeters. It should also be appreciated that instead of a finger glove, other types of fasteners such as tapes, bands, belts, or adhesives on the sensor unit itself may secure the sensor unit.

Figure 18:
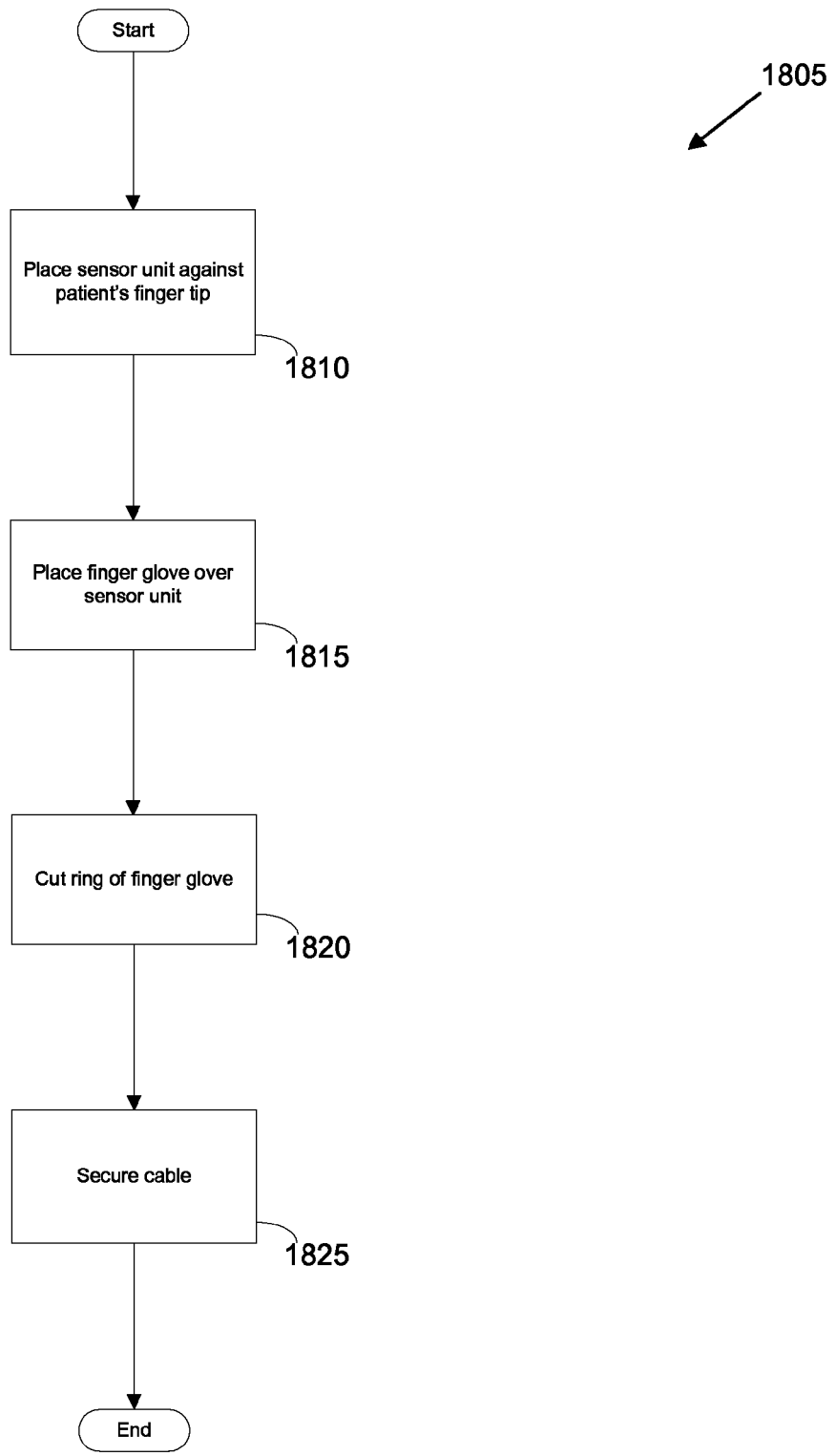
FIG. 18 shows a process flow of a sensor unit without the sensor housing in accordance with a second embodiment of the present invention.

FIG. 18 shows process flow 1805 for using the sensor unit without the sensor housing. In a step 1810, the user places the sensor unit alone against the tip of the patient's finger. The sensor unit is positioned so that the sensor openings contact the patient's skin. In a step 1815, the user covers the sensor unit with the finger glove. The finger glove secures the sensor unit against the patient's fingertip. The finger glove should cover the fingertip and the sensor unit but should not be too constricting. In a specific embodiment, the finger glove only covers the portion of the patient's finger that includes the sensor unit. In other embodiments, the finger glove covers the sensor unit and a portion of the finger past the sensor unit toward the palm.

In a step 1820, the user makes a vertical cut in the ring of the finger glove to reduce blood constriction.

In a step 1825, the user stabilizes the sensor unit's position by fastening the cable to the patient's forearm. In an implementation, the user couples the cable to itself using plastic cable ties. The user then attaches the cable to the patient's forearm using a loose band of material that is easy to remove and does not constrict the skin. This includes, for example, a fabric hook-and-loop fastener, self-sticking gauze, tape, belts, rubber bands, plastic-coated ties, and other fasteners. In other implementations, the cable may not be coupled to itself before it is attached to the forearm. Users may also clip the cable to the patient's clothing, gown, or bedding.

Figure 19:
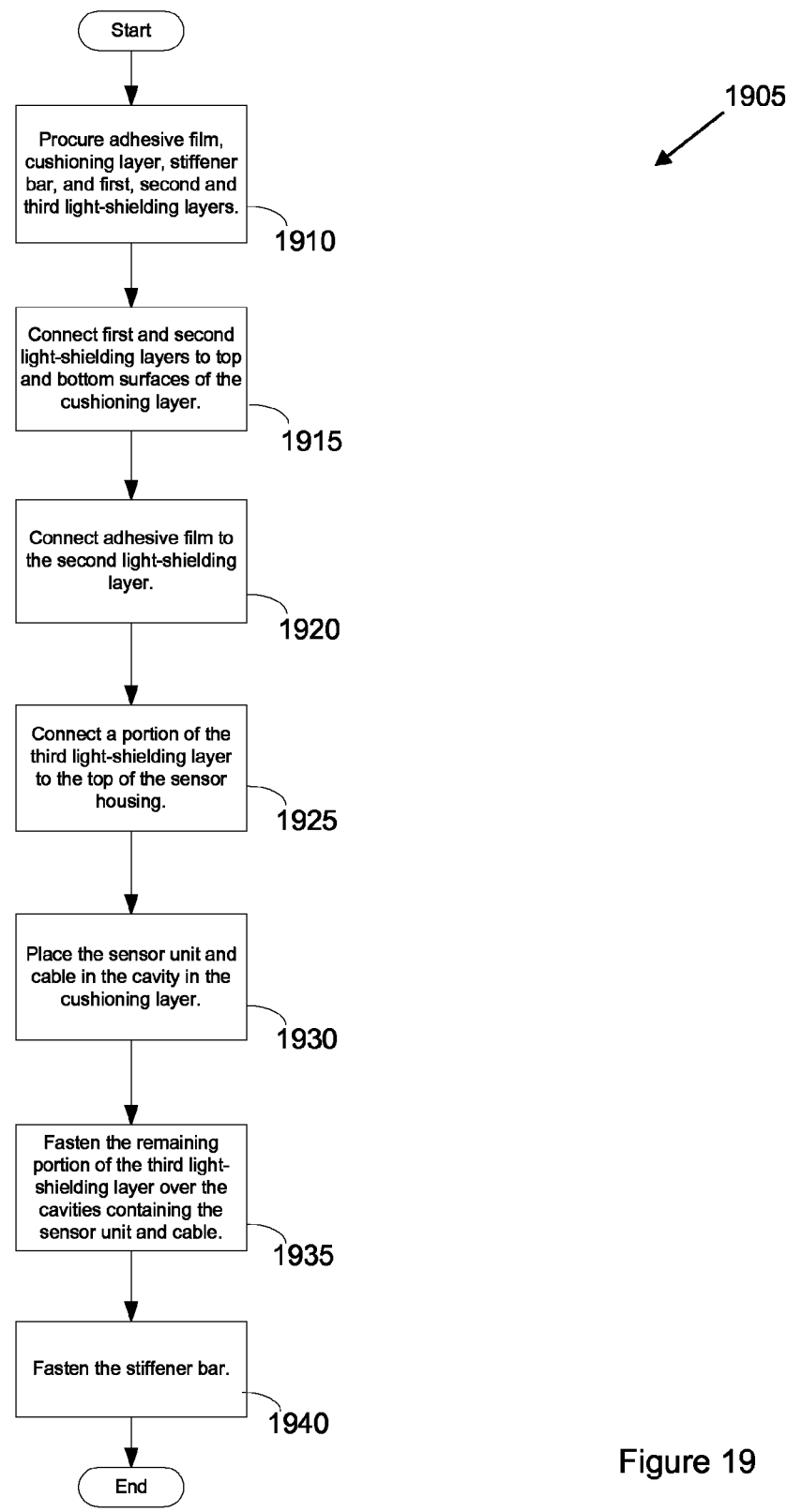
FIG. 19 shows a process flow for manufacturing a sensor housing in accordance with an embodiment of the present invention.

FIG. 19 shows a process 1905 of making the invention. In a step 1910, the manufacturer procures the parts. In a particular embodiment, this includes: the adhesive film (with the release liners), the first, second and third light-shielding layers, the cushioning layer, the stiffener bar, the sensor unit, and the cable.

In a step 1915, the first and second light-shielding layers are coupled to the top and bottom surfaces of the cushioning layer. The first light-shielding layer is coupled such that its cavities overlap the cavities in the cushioning layer. The second light-shielding layer is coupled such that its opening overlaps the cavity in the cushioning layer for the sensor unit.

In a step 1920, the adhesive film is coupled to the second light-shielding layer. The adhesive film forms the base of the sensor housing.

In a step 1925, the third light-shielding layer is partially coupled to the top of the sensor housing. The third light-shielding layer has a multisection release liner. This release liner covers an adhesive on the light-shielding layer. A first portion of the release liner is removed, exposing an adhesive. A first portion of the light-shielding layer is then coupled to the top of the sensor housing. The third light-shielding layer is coupled such that the first portion does not overlap the cavities in the cushioning layer.

This results in an unfastened flap of the third light-shielding layer. Leaving a portion of the third light-shielding layer unfastened allows assembly of the sensor housing independent of the sensor unit. If there is a delay in sourcing parts for the sensor unit, the delay will have minimal impact on assembling the sensor housing. The sensor housing may also be shipped to a different location for installation of the sensor unit. Less protective packing material is needed; the sensor housing does not yet contain any fragile parts such as the sensor unit and cable. The shipping weight is also less than it would be if the sensor unit and cable were installed.

In a step 1930, the sensor housing is attached to the sensor unit. The sensor unit and cable are placed in their respective cavities in the cushioning layer. The sensor unit is positioned to protrude past the bottom surface of the sensor housing. This ensures that the sensor unit contacts the patient's skin.

In a step 1935, a second portion of the release liner for the third light-shielding layer is removed. The adhesive is now exposed. The unsecured flap of the third light-shielding layer is then pressed over the cavities which contain the sensor unit and cable.

Finally, in a step 1940, the stiffener bar is placed above the cavity containing the cable.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A device comprising:
a pad region having a cavity,
wherein the cavity comprises a cavity opening, and the cavity extends from the cavity opening to an inside surface that is opposite of the cavity opening,
the cavity is positioned between a first end of the pad region and a second end of the pad region, opposite the first end, and
a bottom surface area of the pad region is greater than a bottom surface area of the cavity opening;
a first light-shielding layer, coupled to the pad region, wherein the first light-shielding layer has an opening that overlaps with at least a portion of the cavity opening; and
an adhesive layer, coupled to the first light-shielding layer, wherein the adhesive layer extends past at least one edge of the first light-shielding layer.

2. The device of claim 1 comprising:
a sensor unit positioned in the cavity; and
a cable coupled to the sensor unit, wherein the cable is arranged to enter the cavity, the cable being arranged to define a longitudinal axis that passes through the cable and the device, dividing the device into a first side and a second side, wherein the first and second sides are mirror images of each other.

3. The device of claim 2 wherein the cable has a length greater than 1.2 meters.

4. The device of claim 2 wherein the sensor unit comprises:
a first source structure;
a second source structure;
a first detector structure comprising optical fiber; and
a second detector structure comprising optical fiber, wherein a first distance is between the first source structure and the first detector structure, a second distance is between the first source structure and the second detector structure, a third distance is between the second source structure and the first detector structure, a fourth distance is between the second source structure and the second detector structure,
the first distance is not equal to the second, third, and fourth distances, the second distance is not equal to the third and fourth distances, and the third distance is not equal to the fourth distance.

5. The device of claim 2 wherein the sensor unit is bounded on three sides by the pad region.

6. The device of claim 2 wherein a tissue-facing surface of the sensor unit is exposed through the cavity of the pad region.

7. The device of claim 2 wherein a tissue-facing surface of the sensor unit protrudes from the cavity past a bottom surface of the pad region.

8. The device of claim 7 wherein the tissue-facing surface of the sensor unit protrudes a distance from about 0.8 millimeters to about 2 millimeters past the bottom surface of the pad region.

9. The device of claim 1 wherein a bottom surface area of the pad region is greater than a bottom surface area of a sensor unit recessed into the cavity.

10. The device of claim 1 wherein the pad region, first light-shielding layer, and adhesive layer each comprise at least two opposing straight edges which are parallel, the pad region, first light-shielding layer, and adhesive layer being arranged so that the at least two opposing straight edges of the pad region, first light-shielding layer, and adhesive layer overlap, the adhesive layer further comprising:
a left portion having a shape of a semicircle;
a middle portion having a shape of a polygon; and
a right portion having a shape of a semicircle, wherein the middle portion is between the left portion and the right portion.

11. The device of claim 1 wherein the thickness of the pad region when uncompressed is thicker than a sensor unit.

12. The device of claim 1 wherein a stiffener bar is coupled to a top surface of the pad region, above at least a portion of the cavity.

13. The device of claim 1 further comprising a release liner, coupled to the adhesive layer, wherein the release liner comprises a tab positioned along an edge where a cable enters the pad region.

14. The device of claim 1 wherein the adhesive layer is transparent.

15. The device of claim 1 further comprising a second light-shielding layer coupled to a top surface of the pad region, wherein the second light-shielding layer has an opening that overlaps with at least a portion of the cavity.

16. The device of claim 1 wherein a ratio of a thickness of the pad region to a length of the adhesive layer is less than 0.1.

17. The device of claim 1 wherein the pad region has a thickness at least about 3.2 millimeters.

18. The device of claim 1 wherein an edge of the cavity overlaps with an edge of the pad region.

19. The device of claim 1 further comprising a third light-shielding layer, wherein the third light-shielding layer comprises a coupled portion and an uncoupled portion, wherein the coupled portion is coupled to the device and does not overlap the cavity, and the uncoupled portion overlaps the cavity.

20. The device of claim 1 further comprising a second light-shielding layer coupled to a bottom surface of the pad region, wherein the second light-shielding layer has an opening that overlaps with at least a portion of the cavity.

21. The device of claim 1 wherein the bottom surface area of the pad region is about 200 to 700 percent greater than the bottom surface area of the cavity.

22. A device comprising:
a pad region having a cavity, wherein the cavity comprises a cavity opening and an inside surface of the cavity, opposite to the opening;
a first light-shielding layer, coupled to the pad region;
an adhesive layer, coupled to the first light-shielding layer, wherein a peripheral outline forms an outer boundary of the adhesive layer, and all points on a line drawn between any point on the peripheral outline to any other point on the peripheral outline are enclosed by the outer boundary; and
a sensor unit positioned in the cavity, wherein a back of the sensor unit faces the inside surface of the cavity, and at least a portion of the sensor unit is embedded in the pad region, holding the sensor unit therein.

23. The device of claim 22 wherein the adhesive layer comprises:
a first convex edge;
a second convex edge;
a first straight edge; and
a second straight edge,
wherein the first straight edge is parallel to the second straight edge, the first and second straight edges are between the first and second convex edges, the first convex edge is a mirror image of the second convex edge, and a cable, coupled to the sensor unit, crosses one of the first straight edge or second straight edge.

24. The device of claim 23 wherein the cable is transverse to one of the first straight edge or second straight edge.

25. The device of claim 23 wherein the cable crosses the one of the first straight edge or second straight edge at an angle other than 90 degrees.

26. The device of claim 22 comprising:
a cable coupled to the sensor unit, wherein the cable has a length greater than 1.2 meters.

27. The device of claim 22 wherein the adhesive layer is transparent.

28. The device of claim 22 comprising a cable, coupled to the sensor unit, wherein a portion of the cable is surrounded by the pad region.

29. A device comprising:
a sensor unit, wherein the sensor unit comprises a first source structure, a second source structure, a first detector structure, and a second detector structure on a scanning surface of the sensor unit, and a back surface of the sensor unit is opposite of the scanning surface;
a cable coupled to the sensor unit; and
a sensor pad, coupled to the sensor unit, wherein the sensor pad comprises a recessed region that holds the sensor unit, the recessed region has an opening and an inside surface opposite to the opening, and the back surface of the sensor unit is positioned against the inside surface of the recessed region,
a light-shielding layer, having an opening, is coupled to a tissue-facing surface of the sensor pad and extending beyond a first and second edge of the sensor pad in at least two opposite directions, and
the opening overlaps with at least a portion of the sensor unit, and an adhesive layer is coupled to the light-shielding layer and extending beyond a first and second edge of the light-shielding layer in at least two opposite directions.

* * * * *